United States Patent
Gordon et al.

[19]

[11] Patent Number: 6,001,381
[45] Date of Patent: *Dec. 14, 1999

[54] CLEANING ARTICLES COMPRISING A POLARPHOBIC REGION AND A HIGH INTERNAL PHASE INVERSE EMULSION

[75] Inventors: Gregory Charles Gordon, Cincinnati; Larry Neil Mackey, Fairfield; Paul Dennis Trokhan, Hamilton, all of Ohio

[73] Assignee: The Procter & Gamble Company, Cincinnati, Ohio

[*] Notice: This patent is subject to a terminal disclaimer.

[21] Appl. No.: 09/004,001

[22] Filed: Jan. 7, 1998

Related U.S. Application Data

[63] Continuation of application No. 08/759,546, Dec. 5, 1996, Pat. No. 5,763,332, which is a continuation-in-part of application No. 08/640,049, Apr. 30, 1996, abandoned.

[51] Int. Cl.[6] .................................................. A61K 9/70
[52] U.S. Cl. ........................... 424/402; 424/449; 424/486
[58] Field of Search .................................... 424/402, 449; 428/486

[56] References Cited

U.S. PATENT DOCUMENTS

| | | | |
|---|---|---|---|
| 2,868,824 | 1/1959 | Haluska | 260/448.2 |
| 3,215,707 | 11/1965 | Rense | 260/326.3 |
| 3,231,587 | 1/1966 | Rense | 260/346.8 |
| 3,818,533 | 6/1974 | Scheuer | 15/104.93 |
| 3,819,530 | 6/1974 | Ratledge et al. | 252/311.5 |
| 3,847,637 | 11/1974 | Luszczak | 106/271 |
| 3,896,807 | 7/1975 | Buchalter | 128/261 |
| 3,919,149 | 11/1975 | Cushman et al. | 260/28.5 AV |
| 3,965,518 | 6/1976 | Muoio | 15/104.93 |
| 3,982,993 | 9/1976 | Fife | 162/158 |
| 4,043,829 | 8/1977 | Ratledge et al. | 106/271 |
| 4,082,887 | 4/1978 | Coates | 428/289 |
| 4,104,403 | 8/1978 | Barker et al. | 424/365 |
| 4,112,167 | 9/1978 | Dake et al. | 428/154 |
| 4,117,199 | 9/1978 | Gotoh et al. | 428/486 |

(List continued on next page.)

FOREIGN PATENT DOCUMENTS

| | | | |
|---|---|---|---|
| 1 132 908 | 10/1982 | Canada | 167/310 |
| 0 110 678 A2 | 6/1984 | European Pat. Off. | C08K 7/00 |
| 0 259 034 A2 | 3/1988 | European Pat. Off. | A61K 7/00 |
| 0 365 160 A2 | 9/1989 | European Pat. Off. | A61K 7/40 |
| 0 501 791 A3 | 9/1992 | European Pat. Off. | C08G 77/46 |
| 0 545 002 A1 | 6/1993 | European Pat. Off. | C08G 77/46 |
| 0 631 774 A1 | 1/1995 | European Pat. Off. | A61K 9/113 |
| 2 321 389 | 12/1976 | France | B32B 29/02 |
| 2 321 389 | 2/1987 | France | B32B 29/02 |
| 3341770 A1 | 5/1985 | Germany | A61K 9/06 |
| 155758 | 9/1981 | India | A61K 7/00 |
| 2/152920 | 6/1990 | Japan | A61K 7/50 |
| 3/168118 | 7/1991 | Japan | A47L 13/17 |
| 05070337-A | 3/1993 | Japan | A61K 7/48 |
| 9144-426-A | 8/1994 | Japan . | |
| 1059541 | 2/1967 | United Kingdom . | |
| 2 055 689 | 3/1981 | United Kingdom | B32B 3/30 |
| 2055689 | 3/1981 | United Kingdom | B32B 3/30 |

(List continued on next page.)

OTHER PUBLICATIONS

"Dow Corning Q2–5200 Formulation Aid", Dow Corning Corporation (1990).

*Primary Examiner*—Jose' G. Dees
*Assistant Examiner*—Kathryne E. Shelborne
*Attorney, Agent, or Firm*—Carl J. Roof; E. Kelly Linman; Jacobus C. Rasser

[57] ABSTRACT

Wet-like cleaning wipes and similar articles that are particularly useful in removing perianal soils. These wipes comprise a carrier comprising at least one polarpliobic region, an optional, preferred substrate such as tissue paper web, and an emulsion applied to the carrier. The emulsion comprises a continuous external lipid phase and a dispersed internal polar phase. The continuous lipid phase of the emulsion is sufficiently brittle that it ruptures when subjected to low shear pressures during use to release the dispersed internal phase. Inclusion of the polarphobic region allows the ability to control flow of the internal water phase components following rupture of the emulsion.

52 Claims, 4 Drawing Sheets

U.S. PATENT DOCUMENTS

| | | | |
|---|---|---|---|
| 4,122,029 | 10/1978 | Gee et al. | 252/309 |
| 4,137,358 | 1/1979 | Hartz | 428/272 |
| 4,203,877 | 5/1980 | Baker | 260/18 |
| 4,246,423 | 1/1981 | Martin | 556/423 |
| 4,293,611 | 10/1981 | Martin | 428/266 |
| 4,339,276 | 7/1982 | Yokoyama et al. | 106/271 |
| 4,377,649 | 3/1983 | Sweeney et al. | 524/49 |
| 4,381,241 | 4/1983 | Romenesko et al. | 252/8.5 P |
| 4,385,049 | 5/1983 | Cuca | 424/167 |
| 4,421,656 | 12/1983 | Donatelli et al. | 252/8.5 P |
| 4,446,051 | 5/1984 | Berthod et al. | 252/309 |
| 4,468,254 | 8/1984 | Yokoyama et al. | 106/271 |
| 4,481,243 | 11/1984 | Allen | 428/154 |
| 4,513,051 | 4/1985 | Lavash | 428/212 |
| 4,514,345 | 4/1985 | Johnson et al. | 264/22 |
| 4,520,160 | 5/1985 | Brown | 524/765 |
| 4,606,913 | 8/1986 | Aronson et al. | 424/59 |
| 4,698,178 | 10/1987 | Hüttinger et al. | 252/309 |
| 4,708,753 | 11/1987 | Forsberg | 149/2 |
| 4,782,095 | 11/1988 | Gum | 514/937 |
| 4,801,447 | 1/1989 | Gum | 424/68 |
| 4,844,756 | 7/1989 | Forsberg | 149/2 |
| 4,853,474 | 8/1989 | Bahr et al. | 556/445 |
| 4,875,927 | 10/1989 | Tadros | 71/94 |
| 5,021,405 | 6/1991 | Klimisch | 514/63 |
| 5,047,175 | 9/1991 | Forsberg | 252/356 |
| 5,133,972 | 7/1992 | Ferrini et al. | 424/449 |
| 5,136,068 | 8/1992 | Bahr et al. | 556/445 |
| 5,162,378 | 11/1992 | Guthauser | 514/785 |
| 5,210,102 | 5/1993 | Klimisch | 514/784 |
| 5,245,025 | 9/1993 | Trokhan et al. | 536/56 |
| 5,247,044 | 9/1993 | Crivello et al. | 528/15 |
| 5,277,761 | 1/1994 | Van Phan et al. | 162/109 |
| 5,292,503 | 3/1994 | Raleigh et al. | 424/59 |
| 5,362,482 | 11/1994 | Yoneyama et al. | 424/69 |
| 5,378,455 | 1/1995 | Kealey et al. | 424/73 |
| 5,387,417 | 2/1995 | Rentsch | 424/401 |
| 5,470,551 | 11/1995 | Dubief et al. | 424/70.12 |
| 5,482,703 | 1/1996 | Pings | 424/70.12 |
| 5,503,715 | 4/1996 | Trokhan et al. | 162/296 |
| 5,525,345 | 6/1996 | Warner et al. | 424/402 |
| 5,534,326 | 7/1996 | Trokhan et al. | 428/131 |

FOREIGN PATENT DOCUMENTS

| | | | |
|---|---|---|---|
| 2 113 236 | 8/1983 | United Kingdom | C08L 83/12 |
| 87/03613 | 6/1987 | WIPO | C10M 173/00 |
| 94/02120 | 2/1994 | WIPO | A61K 9/113 |
| 95/16824 | 6/1995 | WIPO | D21H 17/14 |
| 96/14835 | 5/1996 | WIPO | A61K 9/70 |

CLEANING ARTICLES COMPRISING A POLARPHOBIC REGION AND A HIGH INTERNAL PHASE INVERSE EMULSION

CROSS REFERENCE TO RELATED APPLICATION

This application is a continuation application os U.S. patent application Ser. No. 08/759,546, filed Dec. 5, 1996, now U.S. Pat. No. 5,763,332, which is a continuation-in-part application of U.S. Pat. application Ser. No. 08/640,049, filed Apr. 30, 1996, now abandoned, by G. Gordon et al.

TECHNICAL FIELD

This application relates to articles that are useful as wet-like cleaning wipes. The application particularly relates to wet-like cleaning wipes made from a carrier treated with a high internal phase inverse emulsion comprising a polar internal phase. The carrier contains a region that inhibits penetration of the polar phase components that adversely affect its in-use strength and integrity, and/or to preferentially force the polar phase to one surface of the wipe in order to maintain a dry second surface. The wipes are useful in various applications, including those for hard surface cleaning and personal cleansing such as baby wipes, and particularly for removal of perianal soils.

BACKGROUND OF THE INVENTION

Cleansing the skin is a personal hygiene problem not always easily solved. Of course, the common procedure of washing the skin with soap and water works well, but at times may be either unavailable or inconvenient to use. While soap and water could be used to clean the perianal region after defecation for example, such a procedure would be extremely burdensome. Dry tissue products are therefore the most commonly used post-defecation anal cleansing product. These dry tissue products are usually referred to as "toilet tissue" or "toilet paper."

The perianal skin is marked by the presence of fine folds and wrinkles (sulci) and by hair follicles which make the perianal region one of the more difficult anatomical areas to cleanse. During defecation, fecal matter is excreted through the anus and tends to accumulate in hard to reach locations such as around the base of hairs and in the sulci of the skin's surface. As the fecal matter dehydrates upon exposure to the air, or upon contact with an absorbent cleansing implement such as tissue paper, it adheres more tenaciously to the skin and hair, thus making subsequent removal of the remaining dehydrated soil even more difficult.

Failure to remove fecal matter from the anal area can have a deleterious effect on personal hygiene. The fecal matter remaining on the skin after post-defecation cleansing has a high bacterial and viral content, is malodorous and is generally dehydrated. These characteristics increase the likelihood of perianal disorders and cause personal discomfort (e.g., itching, irritation, chafing, etc.). Further, the residual fecal matter stains undergarments and causes unpleasant odors to emanate from the anal region. Thus, the consequences of inadequate perianal cleansing are clearly unattractive.

For those individuals suffering from anal disorders such as pruritis ani, hemorrhoids, fissures, cryptitis, or the like, the importance of adequate perianal cleansing takes on heightened significance. Perianal disorders are usually characterized by openings in the skin through which the bacteria and viruses in the residual fecal matter can readily enter. Those people afflicted with anal disorders must, therefore, achieve a high degree of perianal cleansing after defecation or risk the likely result that their disorders will be aggravated by the bacteria and viruses remaining on the skin.

At the same time anal disorder sufferers face more severe consequences from insufficient post defecation cleaning, they have greater difficulty in achieving a satisfactory level of soil removal. Anal disorders generally render the perianal region extremely sensitive and attempts to remove fecal matter from this region by wiping with even normal wiping pressure causes pain and can further irritate the skin. Attempts to improve soil removal by increasing the wiping pressure can result in intense pain. Conversely, attempts to minimize discomfort by reducing the wiping pressure result in an increased amount of residual fecal matter left on the skin.

Conventional toilet tissue products used for anal cleaning are essentially dry, low density tissue papers that rely exclusively on mechanical processes to remove fecal matter from the perianal skin. These conventional products are rubbed against the perianal skin, typically with a pressure of about 1 psi (7 kilopascals) and basically scrape or abrade the fecal matter from the skin. After the first few wipes, the upper portion of the soil layer is removed because the wiping process is able to overcome the soil-soil cohesive forces that exist within the fecal matter. A cleavage is thereby created in the soil layer itself with the upper portion of the fecal layer being removed and the lower portion of the soil remaining adhered to the perianal skin.

Conventional tissue products are absorbent and with each successive wipe the fecal matter becomes increasingly dehydrated, causing it to adhere more tenaciously to the perianal skin and hair and making its removal difficult in the extreme. Pressing the tissue forcefully against the perianal skin will remove more of the fecal matter but is intensely painful for people suffering from anal disorders and can excoriate even normal perianal skin, potentially causing irritation, inflammation, pain, bleeding, and infection.

To improve perianal cleaning, wipes have been developed that are kept in a dispenser and are typically soaked in a reservoir of a moistening solution. Examples of such products include wipes that are often used to clean babies after bowel movements and can have other additives in the moistening solution to soothe the skin. These wipes can have permanent wet strength such that they are not flushable. Also, these prior wipes are often too wet to dry the skin and tend to have a "cold" feel. There is also a lack of consistency in terms of the moisture content of each of the wipes.

Moistenable dry tissue products have also been used in perianal cleaning. These moistenable tissue products usually have temporary wet strength such that they are flushable. However, the users of these products have to separately wet the tissue, which can be inconvenient. It is also difficult to get the desired moisture level with such products. Also, the temporary wet strength of such products is typically inadequate and needs to be improved.

Co-pending U.S. patent application 08/336,456, filed Nov. 9, 1994 by L. Mackey et al., discloses and claims wet-like cleansing wipes that are especially useful in removing perianal soils. These cleansing wipes comprise a substrate material (e.g., a nonwoven) that is treated with a water-in-lipid emulsion. These wipes have a number of significant advantages over prior cleaning products, especially when in the form of wet-like cleansing wipes used to remove perianal soils. These articles release significant quantities of water during use for comfortable, more effective cleaning. The continuous lipid phase of the emulsion is sufficiently brittle so as to be easily disrupted by low shear contact (e.g., during the wiping of the skin) to readily release this internal water phase, but sufficiently tough at elevated temperatures where the lipid is melted to avoid premature release of the water phase during the rigors of processing. The continuous lipid phase of these articles is also sufficiently stable during storage so as to prevent significant evaporation of the internal water phase. The normal tensile strength and flushability properties of these articles are not adversely affected when treated with the high internal phase inverse emulsions of the present invention. As a result, users of these articles get comfortable, efficient, moist cleaning without having to change their normal cleaning habits.

In spite of the significant improvements over prior cleansing wipes, the substrates (also referred to as "carriers") described therein are lacking in one respect. Specifically, because the carriers described are hydrophilic materials, upon shearing of the emulsion in use, a significant amount of water is absorbed into the substrate, and therefore is not available for contact with the item to be cleaned. As such, it is necessary to surf ace treat the substrate with additional amounts of emulsion to account for the level of water absorbed by the carrier.

Accordingly, in certain circumstances, it would be desirable to provide products for cleaning that offer the benefits provided by the cleansing wipes described in tile above co-pending application, but which require treatment with reduced levels of emulsion. This would provide, among other things, simplification of processing the wipes, as well as potential economic advantages since less emulsion would be required to offer the desired wetting effects.

SUMMARY OF THE INVENTION

The present invention relates to articles useful in cleansing, and particularly wet-like cleansing wipes that are especially useful in removing perianal soils. These articles comprise:

a. a carrier comprising a polarphobic region and, optionally, one or more polarphilic substrate layers; and
  b. an emulsion applied to the carrier, the emulsion comprising:
   (1) from about 2 to about 60% of a continuous, solidified external lipid phase comprising a waxy lipid material having a melting point of about 30° C. or higher;
   (2) from about 39 to about 97% of an internal polar phase dispersed in the external lipid phase; and
   (3) an effective amount of an emulsifier capable of forming the emulsion when the external lipid phase is in a fluid state.

The present invention further relates to a method for making these articles. This method comprises the steps of:

A. forming an emulsion comprising:
   (1) from about 2 to about 60% of a continuous external lipid phase comprising a waxy lipid material having a melting point of about 30° C. or higher;
   (2) from about 39 to about 97% of an internal polar phase dispersed in the external lipid phase; and
   (3) an effective amount of an emulsifier capable of forming the emulsion when the external lipid phase is in a fluid state;
  B. applying the emulsion to a carrier at a temperature sufficiently high such that the external lipid phase has a fluid or plastic consistency, the carrier comprising a polarphobic region and, optionally, one or more polarphilic substrate layers; and
  C. cooling the applied emulsion to a temperature sufficiently low such that the external lipid phase solidifies.

The articles of the present invention offer a number of significant advantages over prior cleaning products, especially when in the form of wet-like cleansing wipes used to remove perianal soils. These articles release significant quantities of internal polar phase components (e.g., and preferably, water and aqueous solutions) during use for comfortable, more effective cleaning. The continuous lipid phase of the emulsion is sufficiently brittle so as to be easily disrupted by low shear contact (e.g., during the wiping of the skin) to readily release this internal phase, but sufficiently tough to avoid premature release of the internal polar phase during the rigors of processing. The continuous lipid phase of these articles is also sufficiently stable during storage so as to prevent significant evaporation of the internal polar phase. The normal tensile strength and flushability properties of these articles are not adversely affected when treated with the high internal phase inverse emulsions of the present invention. As a result, users of these articles get comfortable, efficient, moist cleaning without having to change their normal cleaning habits.

Because the carriers used in the articles of the present invention comprise a polarphobic region, the relative amount of polar phase components available at the article's surface(s) after wiping is increased. This is achieved by positioning the polarphobic region such that the internal phase material released upon shearing is not absorbed throughout the thickness, width and/or length of the article, but is instead directed to desired portions thereof. In one aspect, the polarphobic region of the carrier allows the use of the emulsion technology on high density polarphilic carriers by retaining the released polar phase on the article's surface. In one preferred embodiment, the polarphobic region is a discrete layer located in the carrier such that one side of the article will wet under shear, while the other side remains dry for a secondary drying step. That is, in this embodiment, the internal polar phase does not penetrate the entire thickness of the carrier.

Besides perianal cleaning, these articles can be used in many other applications requiring the delivery of polar fluids such as water, as well as actives that arc soluble or dispersible in polar fluids. These include wipes for personal cleansing, such as baby wipes; for hard surface cleaning of floors, countertops, sinks, bathtubs, toilets, and the like; as well as those for the delivery of polar-soluble or dispersible antimicrobial or pharmaceutical actives. These articles can also perform multiple functions. For example, the high internal phase inverse emulsion applied to these articles can be formulated to provide cleaning and waxing benefits at the same time when used on items such as furniture, shoes, automobiles, and the like.

Figure 4:
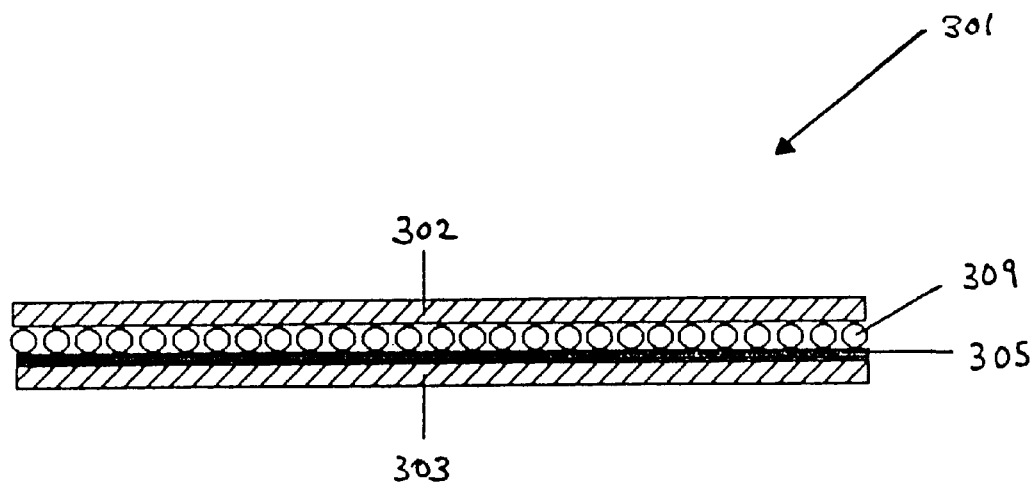
FIG. 4 is a cross-sectional view of another article of the present invention where the internal phase comprises a significant level of water. Article 301 comprises a hydrophobic layer 305 which is a film formed from polyethylene or polypropylene. One surface of hydrophobic layer 305 is treated with emulsion 309. The other side of layer 305 is attached to hydrophilic substrate 303. A second hydrophilic substrate 302 is located on the emulsion layer 309. In this embodiment, in-use pressures cause emulsion 309 to break, thereby releasing internal water phase components, which are allowed to penetrate through hydrophilic layer 302, to one surface of the article. Hydrophobic layer 305 prevents the water phase components from penetrating hydrophilic layer 303. Layer 303 therefore remains dry and can be used to absorb water phase components after wiping.
Figure 5:
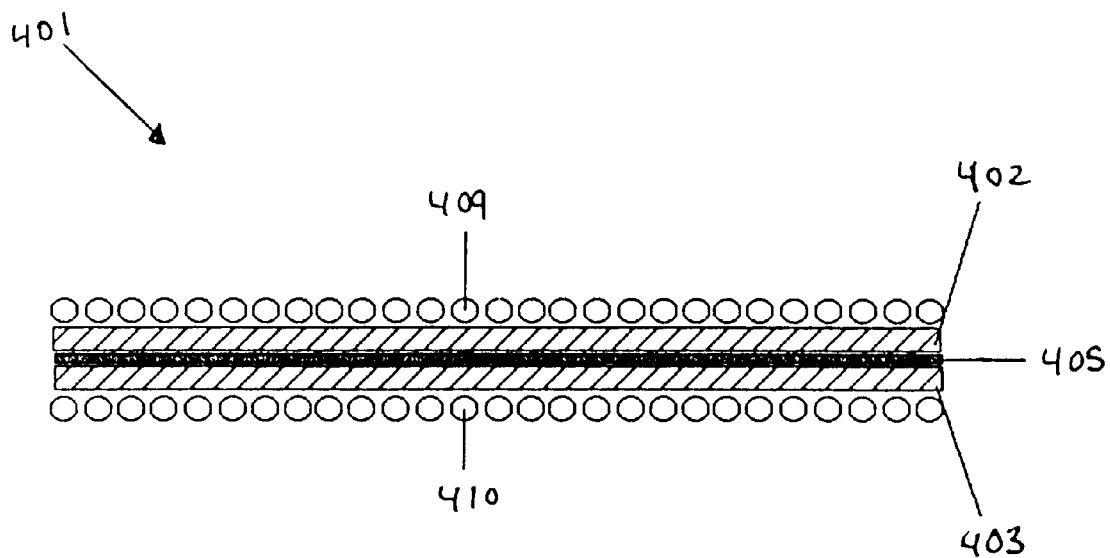
FIG. 5 is a cross-sectional view of another article of the present invention where the internal phase comprises a significant level of water. Article 401 comprises a hydrophobic layer 405 which is a film formed from polyethylene or polypropylene. One surface of hydrophobic layer 405 is attached to a first hydrophilic paper substrate 402. An emulsion layer 409 is applied to hydrophilic substrate 402. The other surface of hydrophobic layer 405 is attached to a second hydrophilic substrate paper 403. Another emulsion layer 410 is applied to hydrophilic substrate 403.
Figure 6:
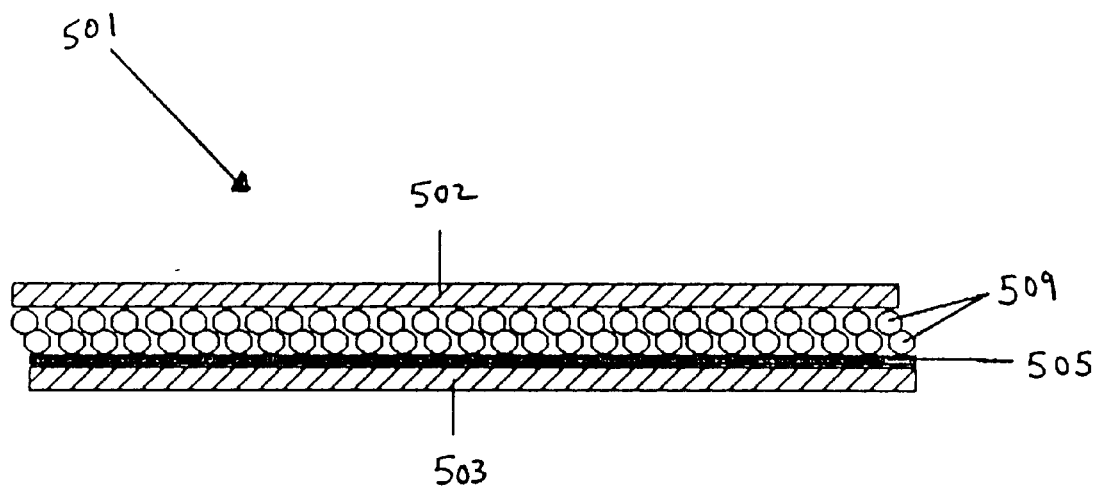
FIG. 6 is a cross-sectional view of another article of the present invention where the internal phase comprises a significant level of water. In this embodiment, article 501 is depicted as comprising a hydrophobic layer 505 which is a film formed from polyethylene or polypropylene. One surface of layer 505 is attached to (hydrophilic) tissue paper 503.

The other surface of layer 505 is coated with a layer of emulsion 509. A second layer of emulsion 509 is coated on a second (hydrophilic) tissue paper 502. Hydrophilic tissue paper 502 is attached to the emulsion-treated surface of hydrophobic layer 505, such that two layers of emulsion 509 are located between tissue 502 and layer 505. This provides a result similar to that exhibited by article 301 of FIG. 4, but with additional emulsion being present because two surfaces are emulsion-treated.

DETAILED DESCRIPTION

As used herein, the term "comprising" means that the various components, ingredients, or steps, can be conjointly employed in practicing the present invention. Accordingly, the term "comprising" encompasses the more restrictive terms "consisting essentially of" and "consisting of."

As used herein, the terms "detergent", "detersive surfactant" and "detergent surfactant" are used interchangeably, and refer to any substance that reduces the surface tension of water, specifically a surface-active agent which concentrates at oil-water interfaces, exerts emulsifying action, and thus aids in removing soils.

As used herein, the term "polar" means a molecule that possesses a dipole moment, i.e., a molecule of which the positive and negative electrical charges are permanently separated, as opposed to a nonpolar molecule in which the charges coincide. A "polar fluid" may comprise one or more polar constituents.

As used herein, the term "polarphilic" is used to refer to surfaces that are wettable by polar fluids deposited thereon. Polarphilicity and wettability are typically defined in terms of contact angle and the surface tension of the fluids and solid surfaces involved. This is discussed in detail in the American Chemical Society publication entitled Contact Angle, Wettability and Adhesion, edited by Robert F. Gould (Copyright 1964), which is hereby incorporated herein by reference. A surface is said to be wetted by a polar fluid (i.e., polarphilic) when either the contact angle between the polar fluid and the surface is less than 90°, or when the polar fluid tends to spread spontaneously across the surface, both conditions normally co-existing. Conversely, a surface is considered to be "polarphobic" if the contact angle is greater than 90° and the fluid does not spread spontaneously across the surface. Since water is generally the preferred polar material used in the present invention, preferred embodiments discussed herein refer to a substrate's "hlydrophilicity" and "hydrophobicity". However, use of such terms is not so limited and should be read to include "polarphilic" and "polarphobic" substrates. Furthermore, the description of a carrier as having polarphobic (and polarphilic) regions necessarily relates to the internal polar phase being employed in the emulsion.

As used herein, the term "hydrophilic" is used to refer to surfaces that are wettable by aqueous fluids deposited thereon. Hydrophilicity and wettability are typically defined in terms of contact angle and the surface tension of the fluids and solid surfaces involved. This is discussed in detail in the American Chemical Society publication entitled Contact Angle, Wettability and Adhesion, edited by Robert F. Gould (Copyright 1964), which is hereby incorporated herein by reference. A surface is said to be wetted by a fluid (i.e., hydrophilic) when either the contact angle between the fluid and the surface is less than 90°, or when the fluid tends to spread spontaneously across the surface, both conditions normally co-existing. Conversely, a surface is considered to be "hydrophobic" if the contact angle is greater than 90° and the fluid does not spread spontaneously across the surface.

As used herein, the terms "substrate" and "layer", when used to describe the carriers of the present invention, refer to a component whose primary dimension is X-Y, i.e., along its length and width. It should be understood that the terms substrate and layer are not necessarily limited to single substrates/layers, or sheets, of material. Thus a substrate or layer can comprise laminates or combinations of several sheets or webs of the requisite type of materials. Accordingly, the term "substrate" includes "substrates", and the term "layer" includes the terms "layers" and "layered."

All percentages, ratios and proportions used herein are by weight unless otherwise specified.

A. Carriers for High Internal Phase Inverse Emulsion

The carriers of the present invention will comprise at least one polarphobic region and, preferably, at least one polarphilic substrate layer. These materials are described in detail below, but are described in terms of their hydrophobicity and hydrophilicity. It is understood that where an emulsion having a polar internal phase comprising significant levels of material(s) other than water, the terms "polarphobic" and "polarphilic", respectively, are intended.

1. Hydophobic Region

The hydrophobic region(s) of the carrier can be generated by either 1) treating a hydrophilic substrate (described below) with a water repellent compound(s) or 2) using a hydrophobic material, such as a thin hydrophobic film or a layer of hydrophobic fibers, as a distinct layer. The preferred design of these products will be a durable hydrophobic region which does not adversely affect the hand feel or softness of the carrier.

When forming the hydrophobic region via surface treatment of a hydrophilic substrate, the hydrophobic material is applied to the substrate by traditional spraying, coating or printing techniques and is then cured through heat and/or ultraviolet sources. (Surface treating with hydrophobic materials is described, for example, in co-pending U.S. patent application Ser. No. 08/442,935, filed May 31, 1995 by W. Ouellette et al. and entitled "Fluid Transport Webs Exhibiting Surface Energy Gradients" (Case 5337R2), which is incorporated herein by reference.) The resulting carrier is a substrate with at least one surface having at least one hydrophobic region. The skilled artisan will recognize that application of the hydrophobic material can be controlled such that numerous discrete, discontinuous hydrophobic regions are provided on the substrate's surface, or the entire surface of the substrate can be treated to provide a continuous hydrophobic layer.

Numerous hydrophobic materials capable of being deposited on a substrate such as a nonwoven are known in the art and are useful herein. Preferred examples include a silicone material from Dow Corning of Midland, Michigan available as Syl-Off 7677 to which a crosslinker available as Syl-Off 7048 is added in proportions by weight of 100 parts to 10 parts, respectively. Another suitable surface treatment is a coating of a UV curable silicone comprising a blend of two silicones commercially available from General Electric Company, Silicone Products Division, of Waterford, N.Y., under the designations UV 9300 and UV 9380C-D1, in proportions by weight of 100 parts to 2.5 parts, respectively. Other suitable materials include, but are not limited to, fluorinated materials such as fluoropolymers (e.g., polytetrafluoroethylene (PTFE), commercially available under the trade name TEFLON®) and chlorofluoropolymers. Other materials which may prove suitable as the hydrophobic material are Petrolatum, latexes, paraffins, and the like, although silicone materials are preferred. Others include any of the commercial water repellents listed in McCutcheon's Volume 2: Functional Materials 1995, McCutcheon's Division, The Manufacturing Confectioner Publishing Co. (the disclosure of which is incorporated by reference herein), of which GrapHsize, available from Akzo Nobel Chemicals Inc., and Norgard 10-T, available from Norman, Fox & Co., are preferred. The necessary addition levels of the hydrophobic compound will be dependent oil the substrate, but will generally fall within the range of from about 1% to about 10% add-on of the dry basis weight of the substrate layer.

The incorporation of a thin film or layer of fibers to provide the hydrophobic region of the carrier can be accomplished by using any type resin which can be extruded to form a hydrophobic film or layer of fibers. Resins useful in forming hydrophobic films/fibers include, but are not limited to, polyolefins such as polyethylene or polypropylene, polyacrylics, polyamides, polystyrenes, polyurethanes and the like. Most preferred are films or fibers derived from polyolefins, preferably polyethylene or polypropylene. The film or fibers may be used as a flat sheet hydrophobic layer and can optionally be attached to a substrate by means of gluing, temperature bonding, or pressure bonding.

Due to the necessity for flexibility of the wipe article to allow for better cleaning, it is desirable to mechanically treat hydrophobic thin films in such a way as to make them more flexible. Ring-rolling is an option which gives a film more flexibility. This technique is described in detail in U.S. Pat. Nos. 5,167,897 to Weber et al. and 5,366,782 to Curro et al., both of which are incorporated herein by reference. An alternative means for achieving flexibility is to utilize a hydrophobic structural elastic-like film (hereinafter referred to as "SELF") web. A structural elastic-like film web is an extensible material that exhibits an elastic-like behavior in the direction of elongation without the use of added elastic materials. SELF webs and techniques for obtaining "SELFed" films are described in the copending, commonly assigned U. S. patent application Ser. No. 08/203,456 entitled "Absorbent Article with Multiple Zone Structural Elastic-Like Film Web Extensible Waist Feature", filed by D. Roe, et al. on Feb. 24, 1994, which is incorporated herein by reference. In addition, a microapertured film allows flexibility while maintaining a hydrophobic barrier against moderate pressure.

Preferred articles are those where the hydrophobic region is either a cross-linked silicone compound applied to all or a portion (preferably all) of one or both (preferably one) surface of the hydrophilic substrate(s), or a mechanically treated thin polymer filn such as ring rolled or SELFed polyethylene.

2. Hydrophilic Substrate Layer

The carriers of the present invention preferably comprise at least one hydrophilic substrate layer. Materials suitable for use as the substrate include woven materials, nonwoven materials, foams, sponges, battings, balls, puffs, films, and the like. Particularly preferred substrates for use in the present invention are nonwoven types. These nonwoven substrates can comprise any conventionally fashioned nonwoven sheet or web having suitable basis weight, caliper (thickness), absorbency and strength characteristics. Nonwoven substrates can be generally defined as bonded fibrous or filamentous products having a web structure, in which the fibers or filaments are distributed randomly as in "air-laying" or certain "wet-laying" processes, or with a degree of orientation, as in certain "wet-laying" or "carding" processes. The fibers or filaments of such nonwoven substrates can be natural (e.g., wood pulp, wool, silk, jute, hemp, cotton, linen, sisal or ramie) or synthetic (e.g., rayon, cellulose ester, polyvinyl derivatives, polyolefins, polyamides or polyesters) and can be bonded together with a polymeric binder resin. Examples of suitable commercially available nonwoven substrates include those marketed under the tradename Sontara® by DuPont and Polyweb® by James River Corp.

For reasons of cost, ease of manufacture and article disposability (e.g., flushability), the preferred type of nonwoven substrate used in wipes of the present invention comprise those made from wood pulp fibers, i.e., paper webs. As noted, paper webs can be prepared by either air-laying or wet-laying techniques. Air-laid paper webs such as Air Tex® SC130 are commercially available from James River Corp.

More conventionally, paper webs are made by wet-laying procedures. In such procedures, a web is made by forming an aqueous papermaking furnish, depositing this furnish onto a foraminous surface, such as a Fourdrinier wire, and by then removing water from the furnish, for example by gravity, by vacuum assisted drying and/or by evaporation, with or without pressing, to thereby form a paper web of desired fiber consistency. In many cases, the papermaking apparatus is set up to rearrange the fibers in the slurry of papermaking furnish as dewatering proceeds in order to form paper substrates of especially desirable strength, hand, bulk, appearance, absorbency, etc.

The papermaking furnish utilized to form the preferred paper web substrates for articles of the present invention essentially comprises an aqueous slurry of papermaking fibers (i.e., paper pulp) and can optionally contain a wide variety of chemicals such as wet strength resins, surfactants, pH control agents, softness additives, debonding agents and the like. Wood pulp in all its variations can be used to form the papermaking furnish. Wood pulps useful herein include both sulfite and sulfate pulps, as well as mechanical, thermo-mechanical and chemi-thermo-mechanical pulps, all of which are well known to those skilled in the papermaking art. Pulps derived from both deciduous or coniferous trees can be used. Preferably the papermaking furnish used to form the preferred paper web substrates for wipes of the present invention comprises Kraft pulp derived from northern softwoods.

A number of papermaking processes have been developed which utilize a papermaking apparatus that forms paper webs having particularly useful or desirable fiber configurations. Such configurations can serve to impart such characteristics of the paper web as enhanced bulk, absorbency and strength. One such process employs an imprinting fabric in the papermaking process that serves to impart a knuckle pattern of high density and low density zones into the resulting paper web. A process of this type, and the papermaking apparatus for carrying out this process, is described in greater detail in U.S. Pat. No. 3,301,746 (Sanford et al), issued Jan. 31, 1967, which is incorporated by reference.

Another papermaking process employs a throughdrying fabric having impression knuckles raised above the plane of the fabric. These impressions create protrusions in the throughdried sheet, and provide the sheet with stretch in the cross-machine direction. A process of this type is described in European Patent Publication No. 677,612A2, published Oct. 18, 1995 by G. Wendt et al., the disclosure of which is incorporated herein by reference.

Still another papermaking process carried out with a special papermaking apparatus, is one that provides a paper web having a distinct, continuous network region formed by a plurality of "domes" dispersed throughout the network region oil the substrate. Such domes are formed by compressing an embryonic web as formed during the papermaking process into a foraminous deflection member having a patterned network surface formed by a plurality of discrete isolated deflection conduits in the deflection member surface. A process of this type, and apparatus for carrying out such a process, is described in greater detail in U.S. Pat. No. 4,529,480 (Trokhan), issued Jul. 16, 1985; U.S. Pat. No. 4,637,859 (Trokhan), issued Jan. 20, 1987; and; U.S. Pat. No. 5,073,235 (Trokhan), issued Dec. 17, 1991, all of which are incorporated by reference. Another type of papermaking process, and apparatus to carry it out that is suitable for making layered composite paper substrates is described in U.S. Pat. No. 3,994,771 (Morgan et al); issued Nov. 30, 1976, which is incorporated by reference.

The preferred paper web substrates can form one of two or more plies that can be laminated together. Lamination, and lamination carried out in combination with an embossing procedure to form a plurality of protuberances in the laminated product, is described in greater detail in U.S. Pat. No. 3,414,459 (Wells); issued Dec. 3, 1968, which is incorporated by reference. These paper substrates preferably have a basis weight of between about 10 g/m² and about 65 g/m², and density of about 0.6 g/cc or less. More preferably, the basis weight will be about 40 g/m² or less and the density will be about 0.3 g/cc or less. Most preferably, the density will be between about 0.04 g/cc and about 0.2 g/cc. See Column 13, lines 61–67, of U.S. Pat. No. 5,059,282 (Ampulski et al), issued Oct. 22, 1991, which describes how the density of tissue paper is measured. (Unless otherwise specified, all amounts and weights relative to the paper web substrates are on a dry weight basis.)

In addition to papermaking fibers, the papermaking furnish used to make these paper web substrates can have other components or materials added thereto are or later become known in the art. The types of additives desirable will be dependent upon the particular end use of the tissue sheet contemplated. For example, in wipe products such as toilet paper, paper towels, facial tissues, baby wipes and other similar products, high wet strength is a desirable attribute. Thus, it is often desirable to add to the papermaking furnish chemical substances known in the art as "wet strength" resins.

A general dissertation on the types of wet strength resins utilized in the paper art can be found in TAPPI monograph series No. 29, Wet Strength in Paper and Paperboard, Technical Association of the Pulp and Paper Industry (New York, 1965). The most useful wet strength resins have generally been cationic in character. For permanent wet strength generation, polyamide-epichlorohydrin resins are cationic wet strength resins that have been found to be of particular utility. Suitable types of such resins are described in U.S. Pat. No. 3,700,623 (Keim), issued Oct. 24, 1972, and U.S. Pat. No. 3,772,076 (Keim), issued Nov. 13, 1973, both of which are incorporated by reference. One commercial source of a useful polyamide-epichlorohydrin resin is Hercules, Inc. of Wilmington, Delaware, which markets such resins under the mark Kymene® 557H.

Polyacrylamide resins have also been found to be of utility as wet strength resins. These resins are described in U.S. Pat. Nos. 3,556,932 (Coscia et al), issued Jan. 19, 1971, and 3,556,933 (Williams et al), issued Jan. 19, 1971, both of which are incorporated by reference. One commercial source of polyacrylamide resins is American Cyanamid Co. of Stamford, Conn., which markets one such resin under the mark Parez® 631 NC.

Still other water-soluble cationic resins finding utility as wet strength resins are urea formaldehyde and melamine formaldehyde resins. The more common functional groups of these polyfunctional resins are nitrogen containing groups such as amino groups and methylol groups attached to nitrogen. Polyethylenimine type resins can also find utility in the present invention. In addition, temporary wet strength resins such as Caldas 10 (manufactured by Japan Carlit), CoBond 1000 (manufactured by National Starch and Chemical Company) and Parez 750 (manufactured by American Cyanamide Co.) can be used in the present invention. It is to be understood that the addition of chemical compounds such as the wet strength and temporary wet strength resins discussed above to the pulp furnish is optional and is not necessary for the practice of the present invention.

In addition to wet strength additives, it can also be desirable to include in the papermaking fibers certain dry strength and lint control additives known in the art. In this regard, starch binders have been found to be particularly suitable. In addition to reducing linting of the paper substrate, low levels of starch binders also impart a modest improvement in the dry tensile strength without imparting stiffness that could result from the addition of high levels of starch. Typically the starch binder is included in an amount such that it is retained at a level or from about 0.01 to about 2%, preferably from about 0.1 to about 1%, by weight of the paper substrate.

In general, suitable starch binders for these paper web substrates are characterized by water solubility, and hydrophilicity. Although it is not intended to limit the scope of suitable starch binders, representative starch materials include corn starch and potato starch, with waxy corn starch known industrially as amioca starch being particularly preferred. Amioca starch differs from common corn starch in that it is entirely amylopectin, whereas common corn starch contains both amylopectin and amylose. Various unique characteristics of amioca starch are further described in "Amioca—The Starch From Waxy Corn," H. H. Schopmeyer, Food Industries, December 1945, pp. 106–108 (Vol. pp. 1476–1478).

The starch binder can be in granular or dispersed form, the granular form being especially preferred. The starch binder is preferably sufficiently cooked to induce swelling of the granules. More preferably, the starch granules are swollen, as by cooking, to a point just prior to dispersion of the starch granule. Such highly swollen starch granules shall be referred to as being "fully cooked." The conditions for dispersion in general can vary depending upon the size of the starch granules, the degree of crystallinity of the granules, and the amount of amylose present. Fully cooked amioca starch, for example, can be prepared by heating an aqueous slurry of about 4% consistency of starch granules at about 190° F. (about 88° C.) for between about 30 and about 40 minutes. Other exemplary starch binders that can be used include modified cationic starches such as those modified to have nitrogen containing groups, including amino groups and methylol groups attached to nitrogen, available from National Starch and Chemical Company, (Bridgewater, N.J.), that have previously been used as pulp furnish additives to increase wet and/or dry strength.

Many of the materials described as useful as the optional hydrophilic substrate layer are inherently hydrophilic. Materials which are not naturally hydrophilic can be treated with any of a variety of hydrophilizing agents well known in the art. Suitable surfactants for hydrophilizing include, for example, ethoxylated esters such as Pegosperse® 200-ML, manufactured by Glyco Chemical, Inc. of Greenwich, Conn., ATMER® 645, manufactured by ICI, glucose amides, tri-block copolymers of ethylene oxide and propylene oxide such as Pluronic® P103, manufactured by BASF, and copolymers of silicone and ethylene glycol such as DC190, manufactured by Dow Corning of Midland, Mich. Surfactants may be applied to the surface of the substrate by spraying, printing, or other suitable methods such as disclosed in U.S. Pat. No. 4,950,264, issued to Osborn on Aug. 21, 1990, the disclosure of which is incorporated herein by reference.

B. High Internal Phase Inverse Emulsion

The articles of the present invention comprise an emulsion that is applied to the carrier. The following describes preferred materials useful in preparing the emulsions. It is understood that where an emulsion having a polar internal phase comprising significant levels of material(s) other than water, the terms "polarphobic" and "polarphilic", respectively, are intended.

Where an optional hydrophilic substrate layer is present, the emulsion will be applied to either or both of the hydrophilic substrate and the hydrophobic region(s). Preferably, the emulsion is applied directly to the hydrophilic substrate.

The emulsion comprises: (1) a continuous solidified external lipid phase; (2) an emulsifier that forms the emulsion when the external lipid phase is fluid; and (3) an interial polar phase dispersed in the external lipid phase. Because the internal phase contains a high level of polar material, this emulsion is typically referred to as a "high internal phase inverse emulsion". This high internal phase inverse emulsion ruptures when subjected to low shear during use, e.g., wiping of the skin or other surface, so as to release the internal polar phase.

1. External Lipid Phase

The continuous solidified external lipid phase provides the essential stabilizing structure for the high internal phase inverse emulsions of the present invention. In particular, this continuous lipid phase is what keeps the dispersed internal polar phase from being prematurely released prior to use of the article, such as during storage.

The continuous external lipid phase can comprise from about 2 to about 60% of the emulsion of the present invention. Preferably, this continuous lipid phase will comprise from about 5 to about 30% of the emulsion. Most preferably, this lipid phase will comprise from about 6 to about 15% of the emulsion.

The major constituent of this continuous lipid phase is a waxy lipid material. This lipid material is characterized by a melting point of about 30° C. or higher, i.e., is solid at ambient temperatures. Preferably, the lipid material has a melting point of about 50° C. or higher. Typically, the lipid material has a melting point in the range of from about 40° to about 80° C., more typically in the range of from about 50° to about 70° C.

Although this waxy lipid material is solid at ambient temperatures, it also needs to be fluid or plastic at those temperatures at which the high internal phase inverse emulsion is applied to the carrier. Moreover, even though the lipid material is fluid or plastic at those temperatures at which the emulsion is applied to the carrier substrate, it should still desirably be somewhat stable (i.e., minimal coalescence of emulsion micro-droplets) for extended periods of time at elevated temperatures (e.g., about 50° C. or higher) that are normally encountered during storage and distribution of the articles of the present invention. This lipid material also needs to be sufficiently brittle at the shear conditions of use of the article such that it ruptures and releases the dispersed internal polar phase. These lipid materials should also desirably provide a good feel to the skin when used in personal care products such as wet-like cleansing wipes and tissue used in perianal cleaning.

Suitable waxy lipid materials for use in the high internal phase inverse emulsion of the present invention include natural and synthetic waxes, as well as other oil soluble materials having a waxy consistency. As used herein, the term "waxes" refers to organic mixtures or compounds that are generally insoluble in polar materials such as water and tend to exist as amorphous or microcrystalline solids at ambient temperatures (e.g., at about 25° C.). Suitable waxes include various types of hydrocarbons, as well as esters of certain fatty acids and fatty alcohols. They can be derived from natural sources (i.e., animal, vegetable or mineral) or they can be synthesized. Mixtures of these various waxes can also be used.

Some representative animal and vegetable waxes that can be used in the present invention include beeswax, carnauba, spermaceti, lanolin, shellac wax, candelilla, and the like. Particularly preferred animal and vegetable waxes are beeswax, lanolin and candelilla. Representative waxes from mineral sources that can be used in the present invention include petroleum-based waxes such as paraffin, petrolatum and microcrystalline wax, and fossil or earth waxes such as white ceresine wax, yellow ceresine wax, white ozokerite wax, and the like. Particularly preferred mineral waxes are petrolatum, microcrystalline wax, yellow ceresine wax, and white ozokerite wax. Representative synthetic waxes that can be used in the present invention include ethylenic polymers such as polyethylene wax, chlorinated naphthalenes such as "Halowax," hydrocarbon type waxes made by Fischer-Tropsch synthesis, and the like. Particularly preferred synthetic waxes are polyethylene waxes.

Besides the waxy lipid material, the continuous lipid phase can include minor amounts of other lipophilic or lipid-miscible materials. These other lipophilic/lipid-miscible materials are typically included for the purpose of stabilizing the emulsion to minimize water loss or improving the aesthetic feel of the emulsion on the skin. Suitable materials of this type that can be present in the continuous lipid phase include hot melt adhesives such as Findley 193-336 resin, long chain alcohols such as cetyl alcohol, stearyl alcohol, and cetaryl alcohol, water-insoluble soaps such as aluminum stearate, silicone polymers such as polydimethylsiloxanes, hydrophobically modified silicone polymers such as phenyl trimethicone, and the like. Other suitable lipophilic/lipid miscible materials include polyol polyesters. By "polyol polyester" is meant a polyol having at least 4 ester groups. By "polyol" is meant a polyhydric alcohol containing at least 4, preferably from 4 to 12, and, most preferably from 6 to 8, hydroxyl groups. Polyols include monosaccharides, disaccharides and trisaccharides, sugar alcohols and other sugar derivatives (e.g., alkyl glycosides), polyglycerols (e.g., diglycerol and triglycerol), pentaerythritol, and polyvinyl alcohols. Preferred polyols include xylose, arabinose, ribose, xylitol, erythritol, glucose, methyl glucoside, mannose, galactose, fructose, sorbitol, maltose, lactose, sucrose, raffinose, and maltotriose. Sucrose is an especially preferred polyol. With respect to the polyol polyesters useful herein, it is not necessary that all of the hydroxyl groups of the polyol be esterified, however disaccharides polyesters should have no more than 3, and more preferably no more than 2 unesterified hydroxyl groups. Typically, substantially all (e.g., at least about 85%) of the hydroxyl groups of the polyol are esterified. In the case of sucrose polyesters, typically from about 7 to 8 of the hydroxyl groups of the polyol are esterified.

By "liquid polyol polyester" is meant a polyol polyester from the hereinafter described groups having a fluid consistency at or below about 37° C. By "solid polyol polyester" is meant a polyol polyester from the hereinafter described groups having a plastic or solid consistency at or above about 37° C. As hereinafter described, liquid polyol polyesters and solid polyol polyesters may be successfully employed as emollients and immobilizing agents, respectively, in emulsions of the present invention. In some cases, solid polyol polyesters may also provide some emolliency functionality.

2. Internal Polar Phase

Typically, the major component of the high internal phase inverse emulsions of the present invention is the dispersed internal polar phase. This internal polar phase can provide a number of different benefits when released. For example, in preferred wet-like cleaning wipes for perianal cleaning, it is this released internal polar (preferably water) phase that provides the primary cleansing action for these wipes. In other products, the released internal polar phase can be used to deliver a variety of active components that are soluble or dispersible in polar liquids (preferably water).

The internal polar phase can comprise from about 39 to about 97% of the emulsion of the present invention. Preferably, the internal polar phase will comprise from about 67 to about 92% of the emulsion. Most preferably, the polar phase will comprise from about 82 to about 91% of the emulsion.

In preferred embodiments, the internal polar phase will comprise water as the main constituent. That is, the emulsion will be a water-in-lipid emulsion. In preferred embodiments, the internal polar phase will contain a significant percentage of water, preferably at least about 60%, by weight of the internal polar phase, more preferably at least about 75%, by weight, still more preferably at least about 85%, by weight. In such embodiments, besides water, the internal water phase can comprise other water-soluble or dispersible materials that do not adversely affect the stability of tile high internal phase inverse emulsion. One such material that is typically included in the internal water phase is a water-soluble electrolyte. The dissolved electrolyte minimizes the tendency of materials present in the lipid phase to also dissolve in the water phase. Any electrolyte capable of imparting ionic strength to the water phase can be used. Suitable electrolytes include the water soluble mono-, di-, or trivalent inorganic salts such as the water-soluble halides, e.g., chlorides, nitrates and sulfates of alkali metals and alkaline earth metals. Examples of such electrolytes include sodium chloride, calcium chloride, sodium sulfate, magnesium sulfate, and sodium bicarbonate. The electrolyte will typically be included in a concentration in the range of from about 1 to about 20% of the water phase.

Other water-soluble or dispersible materials that can be present in the internal water phase include thickeners and viscosity modifiers. Suitable thickeners and viscosity modifiers include water-soluble polyacrylic and hydrophobically modified polyacrylic resins such as Carbopol and Pemulen, starches such as corn starch, potato starch, tapioca, gums such as guar gum, gum arabic, cellulose ethers such as hydroxypropyl cellulose, hydroxyethyl cellulose, carboxymethyl cellulose, and the like. These thickeners and viscosity modifiers will typically be included in a concentration in the range of from about 0.05 to about 0.5% of the water phase.

Other water-soluble or dispersible materials that can be present in the internal water phase include polycationic polymers to provide steric stabilization at the water-lipid interface and nonionic polymers that also stabilize the water-in-lipid emulsion. Suitable polycationic polymers include Reten 201, Kymene® 557H and Acco 711. Suitable nonionic polymers include polyethylene glycols (PEG) such as Carbowax. These polycationic and nonionic polymers will typically be included in a concentration in the range of from about 0.1 to about 1.0% of the water phase.

In addition or alternative to containing water, the internal polar phase may comprise polar materials, including solvents such as ethanol, isopropanol, butanol and hexanol; glycols or substituted glycols such as propylene glycol, butylene glycol or hexylene glycol; polyglycols such as diethylene glycol or triethylene glycol; glycol ethers such as short chain (e.g., C1–C6) derivatives of oxyethylene glycol and oxypropylene glycol, such as mono- and di-ethylene glycol n-hexyl ether, mono-, di- and tri-propylene glycol n-butyl ether; and the like. Also, solvents such as tetrahydrofuran, dimethyl sulfoxide, acetone and other substantially water miscible solvents may be included in the internal polar phase.

3. Emulsifier

Another key component of the high internal phase inverse emulsion of the present invention is an emulsifier. In the emulsions of the present invention, the emulsifier is included in an effective amount. What constitutes an "effective amount" will depend on a number of factors including the respective amounts of the lipid and polar phase components, the type of emulsifier used, the level of impurities present in the emulsifier, and like factors. Typically, the emulsifier comprises from about 1 to about 10% of the emulsion. Preferably, this emulsifier will comprise from about 3 to about 6% of the emulsion. Most preferably, this emulsifier will comprise from about 4 to about 5% of the emulsion. While the singular "emulsifier" is used to describe this component, more than one emulsifier may be used when forming the emulsion. Indeed, as discussed below, it may be desirable to utilize both a primary and a secondary emulsifier when certain materials are employed. Though not intended to limit the scope of the invention, where two emulsifiers are utilized, preferred is where the primary emulsifier comprises from about 1 to about 7%, more preferably from about 2 to about 5%, most preferably from about 2 to about 4%, by weight of the emulsion; and the secondary emulsifier comprises from about 0.5 to about 3%, more preferably from about 0.75 to about 2%, most preferably from about 0.75 to about 1.5%, by weight of the emulsion.

The emulsifier needs to be substantially lipid-soluble or miscible with the lipid phase materials, especially at the temperatures at which the lipid material melts. It also should have a relatively low HLB value. Emulsifiers suitable for use in the present invention have HLB values typically in the range of from about 2 to about 5 and can include mixtures of different emulsifiers. Preferably, these emulsifiers will have HLB values in the range of from about 2.5 to about 3.5.

Emulsifiers suitable for use in the present invention include silicone polymer emulsifiers such as alkyl dimethicone copolyols (e.g., Dow Corning Q2-5200 laurylmethicone copolyol). Such emulsifiers are described in detail in co-pending U.S. patent application Ser. No. 08/430,061, filed Apr. 27, 1995 by L. Mackey (Case 5653), which is incorporated by reference herein.

Other suitable emulsifiers are described in co-pending U.S. patent application Ser. No. 08/336,456, filed Nov. 9, 1994 by L. Mackey et al. (Case 5478), which is incorporated by reference herein. Emulsifiers described therein include certain sorbitan esters, preferably the sorbitan esters of $C_{16}$–$C_{22}$ saturated, unsaturated or branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83), sorbitan monoisostearate (e.g., CRILL® 6 made by Croda), sorbitan stearates (e.g., SPAN® 60), sorbitan trioleate (e.g., SPAN® 85), sorbitan tristearate (e.g., SPAN® 65) and sorbitan dipalmitates (e.g., SPAN® 40). Laurylmethicone copolyol is a particularly preferred emulsifier for use in the present invention. Other suitable emulsifiers described therein include certain glyceryl monoesters, preferably glyceryl monoesters of $C_{16}$–$C_{22}$ saturated, unsaturated or branched chain fatty acids such as glyceryl monostearate, glyceryl monopalmitate, and glyceryl monobehenate; certain sucrose fatty acid esters, preferably sucrose esters of the $C_{16}$–$C_{22}$ saturated, unsaturated, and branched chain fatty acids such as sucrose trilaurate and sucrose distearate (e.g., Crodesta® F10), and certain polyglycerol esters of $C_{16}$–$C_{22}$ saturated, unsaturated or branched fatty acids such as diglycerol monooleate and tetraglycerol monooleate. In addition to these primary emulsifiers, coemulsifiers can be used to provide additional water-in-lipid emulsion stability. Suitable coemulsifiers include phosphatidyl cholines and phosphatidyl choline-containing compositions such as the lecithins; long chain $C_{16}$–$C_{22}$ fatty acid salts such as sodium stearate, long chain $C_{16}$–$C_{22}$ dialipliatic, short chain $C_1$–$C_4$ dialiphatic quaternary ammonium salts such as ditallow dimethyl ammonium chloride and ditallow dimethyl ammonium methylsulfate; long chain $C_{16}$–$C_{22}$ dialkoyl(alkenoyl)-2-hydroxyethyl, short chain $C_1$–$C_4$ dialiphiatic quaternary ammonium salts such as ditallowoyl-2-hydroxyethyl dimethyl ammonium chloride, the long chain $C_{16}$–$C_{22}$ dialiphatic imidazolinium quaternary ammonium salts such as methyl-1-tallow amido ethyl-2-tallow imidazolinium methylsulfate and methyl-1-oleyl amido ethyl-2-oleyl imidazolinium metliylsulfate; short chain $C_1$–$C_4$ dialiphatic, long chain $C_{16}$–$C_{22}$ monoaliphatic benzyl quaternary ammonium salts such as dimethyl stearyl benzyl ammonium chloride, and synthetic phospholipids such as stearamidopropyl PG-dimonium chloride (Phospholipid PTS from Mona Industries). Interfacial tension modifiers such as cetyl and stearyl alcohol for closer packing at the polar internal phase-lipid external interface can also be included.

Preferred emulsifiers useful in making the articles of the present invention include the high viscosity emulsifiers described in co-pending U.S. patent application Ser. No. 08/759,547, filed Dec. 5, 1996 by L. Mackey et al. (Case 6082R), which is incorporated by reference herein. These emulsifiers preferably have a viscosity at 55° C. of at least about 500 centipoise. (Viscosity can be measured using a Lab-Line Instruments Brookfield-type rotating disc viscometer.) That application describes specifically the use of emulsifiers such as those designated by The Lubrizol Corporation (Wickliffe, Ohio) as OS-122102, OS-121863, OS-121864, OS-80541J and OS-80691J, which are reaction products of (i) a hydrocarbyl-substituted carboxylic acid or anhydride (preferably a polyisobutylene-substituted succinic acid or anhydride); and (ii) an amine or alcohol, to form an ester or amide product. The materials, and methods for their manufacture, are described in U.S. Pat. No. 4,708,753, issued Nov. 24, 1987 to Forsberg [see especially Column 3, lines 32–38; and Column 8, line 10, to Column 26, line 68], and U.S. Pat. No. 4,844,756, issued Jul. 4, 1989 to Forsberg, both of which are incorporated by reference herein.

Other materials believed to be useful in the present invention include hydrocarbon-substituted succinic anhydrides such as those described in U.S. Pat. No. 3,215,707, issued Nov. 2, 1965 to Rense; U.S. Pat. No. 3,231,587, issued Jan. 25, 1996 to Rense; U.S. Pat. No. 5,047,175, issued to Forsberg on Sep. 10, 1991; and World Patent Publication Number WO 87/03613, published by Forsberg on Jun. 18, 1987. These publications are all incorporated by reference herein.

Still other materials useful as the emulsifier, particularly as a co-cmulsifier with a high viscosity primary emulsifier, are ABA block copolymers of 12-hydroxystearic acid and polyethylene oxide. Such materials are described in U.S. Pat. No. 4,875,927, issued to T. Tadros on Oct. 24, 1989, which is incorporated by reference herein. A representative material of this class useful as an emulsifier herein is available from Imperial Chemical Industries PLC as Arlacel P135.

While all the above-described materials may be used as a single emulsifier, it may be desired to employ more than one emulsifier when forming the emulsion. In particular, where a high viscosity emulsifier is used, a certain "tacky" feel may result when the treated article is subjected to in-use shear pressures that break the emulsion. In this case, it may be desirable to use a relatively lower viscosity co-emulsifier with the primary emulsifier, to allow use of a lower amount of the main emulsifier, thereby alleviating tackiness. In one preferred embodiment of the present invention, a primary emulsifier available from Lubrizol (i.e., reaction product of polyisobutylene-substituted succinic acid and an amine) and a secondary emulsifier that is an ABA block copolymer of poly-12-hydroxystearic acid and polyethylene oxide (e.g., ICI's Arlacel P135) are used to provide an emulsion with improved water retention levels over time, as well as beneficial reduced tackiness (via reduction in level of primary emulsifier). The skilled artisan will recognize that different desired end-uses will dictate whether multiple emulsifiers are appropriate, and the appropriate relative amounts of each if appropriate. Such a determination will require only routine experimentation by the skilled artisan in view of the present disclosure.

4. Optional Emulsion Components

The high internal phase inverse emulsions of the present invention can also comprise other optional components typically present in moisture containing solutions of this type. These optional components can be present in either the continuous external lipid phase or the internal polar phase and include perfumes, antimicrobials (e.g., antibacterials), pharmaceutical actives, deodorants, opacifiers, astringents, skin moisturizers, and the like, as well as mixtures of these components. All of these materials are well known in the art as additives for such formulations and can be employed in effective, appropriate amounts in the emulsions of the present invention. A particularly preferred optional component that is included in the emulsions of wet-like cleansing wipes according to the present invention is glycerin as a skin conditioning agent.

The emulsion component of the articles of the present invention is described and claimed herein in terms of components (i.e., lipid phase components, internal polar phase components, emulsifier components, etc.), and corresponding amounts of these components, that are present after emulsion formation. That is, when the stable emulsion is formed and applied to the carrier. It is understood, however, that the description (components and amounts) of the emulsion also encompasses emulsions formed by combining the described components and levels, regardless of the chemical identity of the components after emulsification and application to the carrier.

C. Other Optional Wipe Components

Besides the high internal phase inverse emulsion, there are other optional components that can be included in the articles of the present invention, typically for tile purpose of improving the cleaning performance of the article when the internal polar phase of the emulsion is released. Certain of these optional components cannot be present in the emulsion at significant levels (e.g., greater than 2% of the internal polar phase) because they can cause premature disruption of the emulsion. These include various anlionic detergent surfactants that have relatively high HLB values (e.g., HLBs of from about 10 to about 25), such as sodium linear alkylbenzene sulfonates (LAS) or alkyl ethoxy sulfates (AES), as well as nonionic detergent surfactants such as alkyl ethoxylates, alkyl amine oxides, alkyl polyglycosides, zwitterionic detergent surfactants, amnpholytic detergent surfactants, and cationic detergent surfactants such as cetyl trimethyl ammonium salts, and lauryl trimethyl ammonium salts. See U.S. Pat. No. 4,597,898 (Vander Meer), issued Jul. 1, 1986 (herein incorporated by reference), especially columns 12 through 16 for representative anionic, nonionic, zwitterionic, ampholytic and cationic detergent surfactants. Instead, these high HLB detergent surfactants can be applied or included in the article separately from the emulsion. For example, an aqueous solution of these high HLB detergent surfactants can be applied to the carrier either before or after application of the emulsion to the carrier. During wiping, the emulsion is disrupted, releasing the internal polar phase (e.g., water) so that it can then be combined with the high HLB detergent surfactant to provide improved hard surface cleaning.

Though the description of the invention generally relates to applying a single emulsion to the carrier, it is recognized that two or more different emulsions may be utilized in preparing a single article. In such embodiments, the emulsions may differ in a variety of ways, including but not limited to the ratio of the internal polar phase and the external lipid phase, the emulsifiers used, the components used for either or both of the internal and lipid phases, and the like. Utilization of multiple emulsions in one article may be particularly desirable when two or more components are incompatible with each other, but can each be included in separate emulsions. Alternatively, if a particular reaction is desired at the time of use, reactants can be provided in separate emulsions. Upon shearing of the emulsions during use, the desired reaction will occur. For example, where foaming is desired during the wiping processes, a mild acid can be incorporated in the internal polar phase of one emulsion, while bicarbonate is incorporated in the internal polar phase of a second emulsion. Upon shearing of the emulsions during use, the reactants interact to provide the desired foam.

D. Preparation of Emulsion Treated Articles

In preparing the articles according to the present invention, the high internal phase inverse emulsion is initially formulated. Typically, this is achieved by blending or melting together the lipid phase components and the emulsifier. The particular temperature to which this lipid/emulsifier mixture is heated will depend on the melting point of the lipid phase components. Typically, this lipid/emulsifier mixture is heated to a temperature in the range from about 50° to about 90° C., preferably from about 70° to about 80° C., prior to being mixed, blended or otherwise combined with the water phase components. The melted lipid/emulsifier mixture is then blended with the polar phase components and then mixed together, typically under low shear conditions to provide the emulsion.

This high internal phase inverse emulsion is then applied in a fluid or plastic state at the temperatures indicated above to the carrier, e.g., a paper web laminated to a polarphobic material. Any of a variety of methods that apply materials having a fluid or plastic consistency can be used to apply this emulsion. Suitable methods include spraying, printing (e.g., flexographic or screen printing), coating (e.g., gravure coating), extrusion, or combinations of these application techniques, e.g. spraying the detergent surfactant on the paper web, followed by gravure coating of the emulsion on the detergent treated web.

The emulsion can be applied either to one or both surfaces of the carrier, or it can be applied to the inner surface(s) of the plies that makes up the carrier. For example, in the case of a two ply carrier wherein the hydrophilic substrate is a paper web with an internal surface treatment of GrapHsize (Akzo Chemicals Inc.) to provide a hydrophobic layer, the emulsion can be applied to the inner surface of the paper web, leaving the outside surface of the paper web free of the emulsion. This carrier design minimizes transfer of wax and emulsifier to the skin of the user which is especially desirable when higher loadings of emulsion are used to provide more liquid for cleaning. For example, to provide the level of liquid of a typical baby wipe, a loading of emulsion of three times the weight of the carrier might be used. The application of the emulsion to both sides of the paper web substrate can be either sequential or simultaneous. Once the emulsion has been applied to the substrate, it is allowed to cool and solidify to form a solidified, typically discontinuous coating or film on the surface of the substrate.

Three ply wipes can be made with the center ply being a hydrophobic barrier and the outer plies being hydrophilic paper webs. Emulsion can be applied to the inner surface of an outer ply (i.e., substrate) and/or to a surface of the center barrier (hydrophobic) ply and the user will have a wipe with one side being wet in use and the other side can be used for drying. Even in a package of wipes, the drying side of the wipe will remain dry because the aqueous fluid is not free to migrate as in non-encapsulated wet wipes.

When a paper web is used as a hydrophilic substrate, the high internal phase inverse emulsion is typically applied to the paper web after the web has been dried, i.e. a "dry web" addition method. The emulsion can be applied nonuniformly to the surface(s) of the materials that make up the carrier. By "nonuniform" is meant that the amount, pattern of distribution, etc. of the emulsion can vary over the surface(s) of the material being treated. For example, some portions of the surface of a paper web can have greater or lesser amounts of the emulsion, including portions of the surface that do not have any emulsion. The high internal phase inverse emulsion can be applied to the paper web at any point after it has been dried. For example, the emulsion can be applied to the paper web after it has been creped from a Yankee dryer. Usually, it is preferred to apply the emulsion to the paper web as it is being unwound from a parent roll and prior to being wound up on smaller, finished product rolls.

Figure 1:
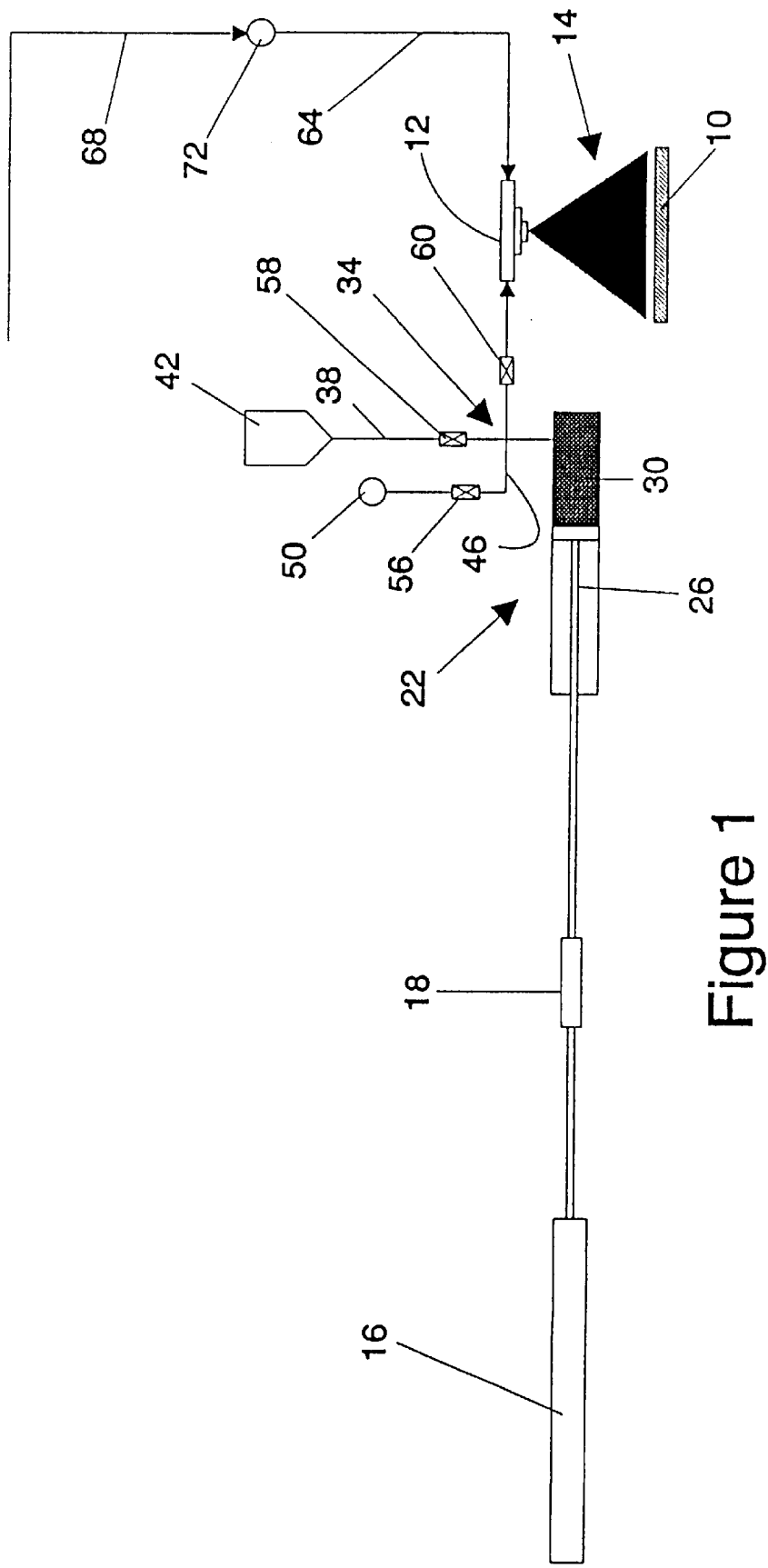
FIG. 1 is a schematic representation illustrating a spray system for applying the high internal phase inverse emulsions of the present invention to a carrier substrate such as a paper web.

In applying high internal phase inverse emulsions to the carriers, spray and gravure coating methods are usually preferred. FIG. 1 illustrates one such preferred method where the emulsion is sprayed onto a carrier 10. Referring to FIG. 1, this spray system has a spray head 12 that applies a dispersed spray 14 of the emulsion onto carrier 10.

This spray system is actuated by an assembly that consists of a ball screw drive 16 that is connected by coupling 18 to a piston 26 of hydraulic cylinder 22. A portion of cylinder 22 is shown in FIG. 1 as being filled with the high internal phase inverse emulsion as indicated by 30. Cylinder 22 is heated to keep emulsion 30 in a fluid or plastic state. Emulsion 30 enters cylinder 22 via a 4-way coupling 34 that has a line 38 connected to a heated filling port 42. Coupling 34 also has a line 46 that is connected to pressure gauge 50 and spray head 12. There are three valves indicated as 56, 58 and 60 that control the flow of the emulsion in lines 38 and 46. The spray system shown in FIG. 1 also has a line 64 connected to spray head 12 that allows air indicated generally as 68 to be admitted to the spray head. Line 64 also has a pressure gauge and regulator 72 for controlling and measuring the air pressure in line. Lines 64 and 46 are heated to maintain the emulsion in a molten state prior to application to the carrier.

To fill cylinder 22 with emulsion 30, valves 56 and 60 are closed and valve 58 is opened. Ball screw drive 16 is actuated so that piston 26 moves to the left. The vacuum created in cylinder 22 draws the emulsion from filling port 42 through line 38 and into cylinder 22. To provide emulsion from cylinder 22 to spray head 12, valve 58 is closed and valves 56 and 60 are opened. The ball screw drive 16 is actuated so that piston 26 moves to the right. This forces emulsion 30 out of cylinder 22 and into line 46 of coupling 34. The emulsion then passes through valve 60 and into the spray head 12 where it is dispersed by incorporation of air from line 64 to provide dispersed spray 14 that is then applied to carrier 10.

Figure 2:
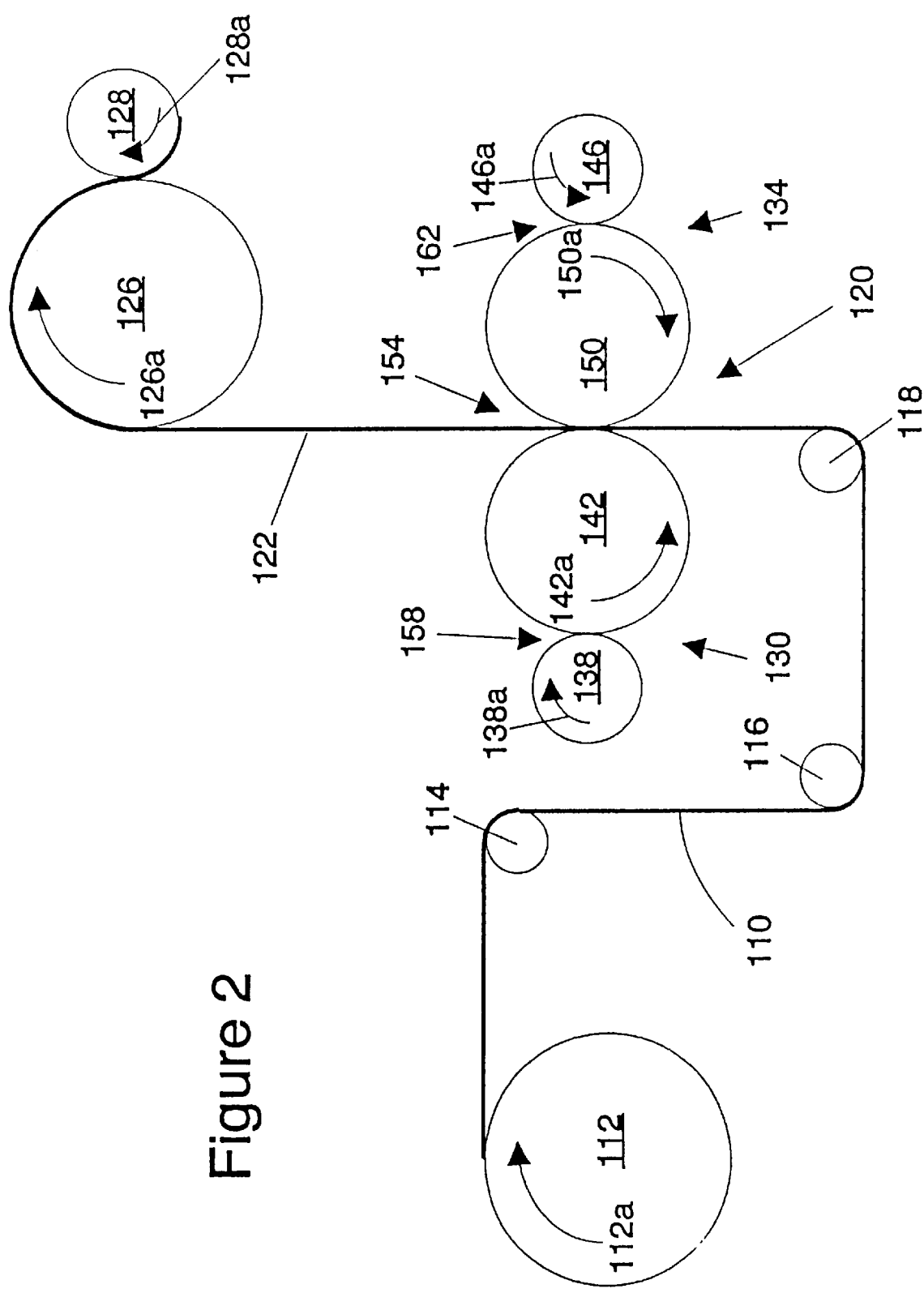
FIG. 2 is a schematic representation illustrating a system for applying the high internal phase inverse emulsions of the present invention by flexible rotogravure coating to a carrier substrate such as a paper web.
Figure 3:
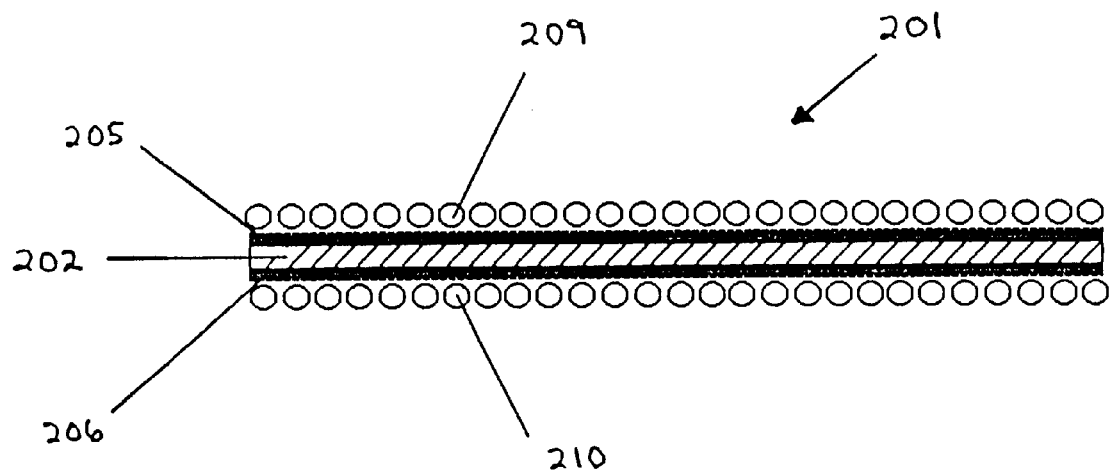
FIG. 3 is a cross-sectional view of an article of the present invention where the internal phase comprises a significant level of water. In this embodiment, article 201 comprises a hydrophilic sheet 202 treated on one of its surfaces with a hydrophobic material to form hydrophobic layer 205, and treated on the other surface with a hydrophobic material to form hydrophobic layer 206. A first emulsion layer 209 is located on hydrophobic layer 205, and a second emulsion layer 210 is located on hydrophobic layer 206. In one embodiment, hydrophobic layers 205 and 206 are continuous, and are formed by treating both sides of sheet 202 with 5% w/w of Syloff 7677 and Syloff 7048 crosslinker in a 95/5 weight ratio, available from Dow Corning Corp., Midland, Mich.

FIG. 2 illustrates an alternative method for applying the high internal phase inverse emulsion involving a flexible rotogravure coating system. Referring to FIG. 2, a carrier 110 is unwound from parent tissue roll 112 (rotating in the direction indicated by arrow 112a) and advanced around turning rolls 114, 116 and 118. From turning roll 118, carrier 110 is advanced to a gravure coating station indicated generally as 120 where the emulsion is then applied to both sides of the carrier. After leaving station 120, carrier 110 becomes a treated web indicated by 122. Treated web 122 is advanced to surface rewinder roll 126 (rotating in the direction indicated by arrow 126a) and then wound up on finished product roll 128 (rotating in the direction indicated by arrow 128a).

Station 120 comprises a pair of heated linked gravure presses 130 and 134. Press 130 consists of a smaller anilox cylinder 138 and a larger print plate cylinder 142; press 134 similarly consists of a smaller anilox cylinder 146 and a larger print plate cylinder 150. Anilox cylinders 138 and 146 each have a ceramic or chrome surface, while print plate cylinders 142 and 150 each have a relief patterned rubber, urethane, or photopolymer surface. These anilox and print plate cylinders rotate in the directions indicated by arrows 138a, 142a, 146a and 150a, respectively. As shown in FIG. 2, print plate cylinders 142 and 150 are opposed to one another and provide a nip area indicated by 154 through which carrier 110 passes.

Hot, molten (e.g., 60° C.) emulsion is pumped to or sprayed onto each of these linked gravure presses 130 and 134 at the nip areas indicated by arrows 158 and 162, respectively, at a constant volumetric flow rate. (Emulsion delivered to presses 130 and 134 may be the same or different.) In other words, the emulsion is added to the linked gravure presses 130 and 134 at the same rate as the emulsion is being applied to the carrier 110. This eliminates emulsion "build-up" in the system. As anilox cylinders 138 and 146 rotate in the directions indicated by arrows 138a and 146a, they act as rotating doctor blades to spread the emulsion evenly across the surfaces of print plate cylinders 142 and 150, respectively, and to remove excess emulsion from the print plates of cylinders 142 and 150.

The emulsion that is spread onto print plate cylinders 142 and 150 (rotating in the opposite direction as indicated by arrows 142a and 150b) is then transferred to both sides of carrier 110 at nip area 154. The amount of the emulsion transferred to carrier 110 can be controlled by: (1) adjusting the width of nip area 154 between print plate cylinders 142 and 150; (2) adjusting the width of nip areas 158 and 162 between anilox/print plate cylinder pairs 138/142 and 146/150; (3) the print image relief (i.e., valley depth) of the print plate on cylinders 142 and 150; (4) the print area (i.e., valley area) of the print plate on cylinders 142 and 150; and/or (6) the print pattern of the print plate on cylinders 142 and 150.

E. Specific Illustrations of the Preparation of Wet-Like Cleaning Wipes According to the Present Invention The following are specific illustrations of the preparation of wet-like cleaning wipes in accordance with the present invention.

EXAMPLE I

This example illustrates preparation of an article comprising a paper substrate that is treated on one or both surfaces with a silicone polymer to provide hydrophobic regions. The emulsion is an emulsion, which is added to either or both sides of the carrier.

A) Emulsion Preparation

An emulsion (86.5% internal phase) is prepared from the ingredients shown in Table I.

TABLE I

|  | Amount (gm) | Percentage |
|---|---|---|
| Lipid Phase Ingredients | | |
| Yellow Ceresine Wax (Strahl & Pitsch SP983) | 350 | 7% |
| Petrolatum (Fisher) | 50 | 1% |
| Dow Corning Q2-5200 emulsifier | 150 | 3% |
| Sorbitan trioleate emulsifier Span ® 85 from ICI) | 100 | 2% |
| Dow Corning 200 dimethicone fluid (350 cSt) | 25 | 0.5% |
| Polar Phase Ingredients | | |
| Dantogard (preservative from Lonza) | 25 | 0.5% |
| Distilled Water | 4300 | 86% |

In formulating the internal aqueous phase component, the Dantogard is added to the distilled water and then heated to 160° F. (71.1° C.). Separately, the lipid phase ingredients (Yellow ceresine wax, petrolatum, Dow Coming 200 fluid, emulsifier Dow Corning Q2-5200 and emulsifier Span 85) are heated, with mixing, to a temperature of about 170° F. (77° C.) until melted. The internal polar phase and external lipid phase components are then combined in a stainless steel vessel and mixed with a Hobart Model 100-C mixer on the low speed setting while allowing the ingredients to cool slowly. Mixing is continued until the emulsion forms. Emulsion formation is evidenced by an increase in viscosity above 2000 centipoise as measured with a Lab-Line Instruments rotating disc viscometer.

B) Carrier Preparation

The carrier is formed by treating a hydrophilic substrate with a polarphobic material. The substrate is a conventional tissue paper substrate. The base paper is a 70/30 Eucalyptus/NSK, non-layered sheet with a basis weight of 21.5 lbs/ream. This paper is unwound through a gravure printing roll which applies Syloff 7677 polymer and Syloff 7048 crosslinker (Dow Coming) in a 95% to 5% blend. The Syloff blend is applied at 5% of the dry substrate basis weight. This application is performed on only one side, or the carrier is passed through another printer to apply the same treatment to both sides of the carrier. The Syloff is then cross-linked through the addition of heat by passing the carrier through two oven zones to provide hydrophobic regions to the carrier. The carrier is now ready for emulsion addition.

C) Applying Emulsion to Carrier

The emulsion prepared in Step A can be applied using the spray system shown in FIG. 1. The emulsion is heated to temperature of 60° C. so that it is fluid or molten. The ball screw drive 16 moves at linear velocity of 0.002 in/sec as it actuates piston 26 (3.5 in. diameter) to push the emulsion out of cylinder 22 (emulsion pressure at about 12 psig). The emulsion enters spray head 12 (external mixing spray head with spray setup SUE15 from Spray Systems Inc., Wheaton, Ill.) and is dispersed in air (at 1.2 psig) heated to about 60° C. The emulsion is then applied from head 12 as a dispersed spray to the carrier while the carrier is being rewound at about 28 ft/min. For example, the carrier can be sprayed at the nip between a rewinder roll and finished product (such as at the nip between surface rewinder roll 126 and finished parent roll 128 shown in FIG. 2). As a result, the emulsion coats both sides of the carrier at about 50% add-on, by dry weight of the carrier.

The emulsion can also be applied to the carrier using the flexible rotogravure coating system shown in FIG. 2. The hot, molten (e.g., 60° C.) emulsion is pumped to or sprayed onto each of these of linked gravure presses 130 and 134 at the nip areas indicated arrows by 158 and 162, respectively, at a constant volumetric flow rate of 20 ml/min. Anilox cylinders 138 and 146 spread the emulsion evenly across the surfaces of print plate cylinders 142 and 150, respectively (each rotating at about 40 feet/minute). Cylinders 142 and 150 then transfer the emulsion to both sides of carrier 110. The coated carrier 122 is transferred to surface rewinder roll 126 such that the coated central width of carrier 122 is over the depressed print area of roll 126. As a result, the coated central width of carrier 122 is not in contact with the surface of roll 126, while the noncoated edges of carrier 122 are in contact with the surface of roll 126. The carrier 122 is then wound up on finished product roll 128. The emulsion coats both sides of carrier 122 at about 50% add-on, by dry weight of the carrier, to provide an article of the present invention.

EXAMPLE II

This example illustrates preparation of an article comprising a polyethylene film (i.e., polarphobic layer) treated on one side with an emulsion. This treated film is located between two paper substrates, to provide an article that is wetted on only one side when subjected to shear forces. The remaining dry side can absorb liquid remaining after use.

A) Emulsion Preparation

An emulsion (88% internal phase) is prepared from the ingredients shown in Table II.

TABLE II

|  | Amount (gm) | Percentage |
|---|---|---|
| Lipid Phase Ingredients | | |
| Yellow Ceresine Wax (Strahl & Pitsch SP983) | 18 | 6% |
| Petrolatum (Fisher) | 3 | 1% |
| White Ozokerite Wax (Strahl & Pitsch SP1190 | 6 | 2% |
| Lubrizol OS#121864 emulsifier | 9 | 3% |
| Polar Phase Ingredients | | |
| 0.1% Carbopol 940* in distilled water adjusted to pH 6.0 with NaOH | 264 | 88% |

*Carbopol ® is an acrylate thickener available from B. F. Goodrich.

The lipid phase ingredients (yellow ceresine wax, petrolatum, white ozokerite wax) and emulsifier (Lubrizol OS#121864) are heated and stirred in a 500 ml stainless steel beaker to a temperature of about 180° F. (82.8° C.) until melted. Separately, the polar phase component is prepared by adding 0.5 gm of Carbopol® 940 and 499.5 gm of distilled water to a 1 liter glass beaker, followed by mixing until the Carbopol® 940 is completely dissolved. The pH of this aqueous solution is adjusted to 6.0 with an appropriate amount of 1N NaOH. A portion (264 gm) of this aqueous solution is added to the beaker containing the lipid phase component. The combined mixture is heated to 160° F. (71° C.) and then mixed with a "Lightnin' TS2510" mixer at 500 rpm while allowing the ingredients to cool until the emulsion forms.

B) Emulsion Application/Carrier Preparation

The emulsion of Step A) is applied to one side of a polarphobic film of ring rolled polyethylene, by either spraying or flexible rotogravure coating according to the procedures of Example I.

The emulsion-treated film is positioned between two hydroentangled substrate layers, each substrate being composed of about 40% natural fibers and about 60% polypropylene fibers (available from Fibertech). The overall basis weight of each of the two outer substrates is about 30 gsm.

The carrier is then passed through a printing station where a continuous coating of General Electric Co. UV9300 silicone release polymer and UV9310C photoinitiator, in a ratio of 98%/2%, is applied. The carrier is then passed under a UV light source for cross-linking to form an article of the present invention.

EXAMPLE III

This example illustrates preparation of an article comprising a polyethylene film (i.e., hydrophobic layer) located between two paper substrates. An emulsion is applied to the outer surface of one or both of the paper substrates.

A) Emulsion Preparation Anemulsion (91% internal phase) is prepared from the ingredients shown in Table Table III.

TABLE III

|  | Amount (gm) | Percentage |
| --- | --- | --- |
| Lipid Phase Ingredients |  |  |
| Yellow Ceresine Wax (Strahl & Pitsch SP983) | 18 | 6% |
| Arlacel P135 emulsifier | 6 | 2% |
| Sorbitan triooleate emulsifier (Span 85 ® from ICI Specialties) | 3 | 1% |
| Polar Phase Ingredients |  |  |
| Sodium Chloride | 21 | 7% |
| Distilled Water | 252 | 84% |

The lipid phase ingredients (yellow ceresine wax, emulsifier Span® 85 and co-emulsifier Arlacel P135) are heated to about 160° F. (71° C.) and mixed in a 500 ml stainless steel beaker until melted. The polar phase ingredients (sodium chloride and distilled water) are added to the beaker containing the lipid phase ingredients. The mixture is heated to 160° F. (71° C.) and then mixed using a "Lightnin' TS2510" mixer at 500 rpm. The mixture is allowed to cool until the emulsion forms.

B) Carrier Preparation

The carrier is composed of a polarphobic polyethylene film sheet located between a first and second tissue substrate. Each of the tissue substrates is a standard tissue web described in Example 1. The polarphobic sheet is a 1 mil polyethylene film from Tredegar Film Products, Terra Haute, IN.

The first tissue web is unwound and passed through a printer which contains a standard plying glue. The polyethylene film is then brought together with the first tissue web to form a laminate structure. Finally a second tissue web treated with the same glue is plied to the opposite side of the laminate structure to produce a carrier with a poly center and tissue on both the outer surfaces. This carrier is then ready for emulsion application.

C) Applying Emulsion to Substrate

The emulsion is applied to one or both outer sides of the carrier by either spraying or flexible rotogravure coating according to the procedures of Example I.

EXAMPLE IV

This example illustrates preparation of an article comprising a polyethylene film (i.e., polarphobic layer) treated on one side with an emulsion. This treated film is located between a tissue paper substrate and a nonwoven substrate that is also treated on one side with the emulsion. Thus, the article has the emulsion sandwiched between the polyethylene film and the nonwoven substrate. This article is wetted on only one side when subjected to shear forces. The remaining dry side (i.e., tissue side) can absorb liquid remaining after use.

A) Emulsion Preparation

An (88% internal phase) is prepared from the ingredients shown in Table IV.

TABLE IV

|  | Amount (gm) | Percentage |
| --- | --- | --- |
| Lipid Phase Ingredients |  |  |
| Paraffin wax (Aldrich) | 9 | 9% |
| Lubrizol OS#121864 emulsifier | 3 | 3% |
| Polar Phase Ingredients |  |  |
| Calcium chloride dihydrate (EM Science) | 4 | 4% |
| Distilled Water | 84 | 84% |

The lipid phase ingredients (paraffin wax and Lubrizol OS#121864 emulsifier) are heated to about 140° F. (60° C.) and mixed in a 500 ml stainless steel beaker until melted. The remaining polar phase ingredients (calcium chloride and distilled water) are added to the beaker containing the lipid phase ingredients. The mixture is heated to 140° F. (60° C.) and then mixed using a "Lightnin' TS2510" mixer at 500 rpm. The mixture is allowed to cool until the emulsion forms.

B) Carrier Preparation/Emulsion Application

The carrier employed is composed of three distinct layers. The first layer is a tissue substrate, as described in Example 1. This tissue is passed through a printer section and a 0.5 mil microapertured (1/10,000 holes) polyethylene film is plied to this tissue by means of glue. Emulsion from Step A) is applied to the microapertured polyethylene film side of the laminate, via spraying or printing. The third layer is a non-woven substrate supplied by Fibertech, comprising 40%/60% cotton/polypropylene). Emulsion from Step A) is also applied to one side of the non-woven substrate, and then the two emulsion containing layers are plied through heat and pressure to bond the synthetic fibers such that emulsion is sandwiched between the polyethylene film and the nonwoven substrate.

EXAMPLE V

This example illustrates the preparation of an article comprising an emulsion applied to a substrate similar to that described in Example IV above. The article is particularly suitable as a wipe for cleaning hard surfaces.

A) Emulsion Preparation

An emulsion having 87% internal polar phase (consisting primarily of water) is prepared from the ingredients shown in Table V.

TABLE V

|  | Amount (gm) | Percentage |
| --- | --- | --- |
| Lipid Phase Ingredients: |  |  |
| Strahl & Pitsch SP983 | 24 | 8.0 |
| Petrolatum | 6 | 2.0 |
| Dow Q2-5200 | 9 | 3.0 |

TABLE V-continued

| | Amount (gm) | Percentage |
|---|---|---|
| Polar Internal Phase Ingredients: | | |
| Distilled Water | 617.76 | 77.22 |
| HEDP | 0.16 | 0.02 |
| Hydrogen Peroxide | 5.6 | 0.7 |
| Ethanol | 69.6 | 8.7 |
| C-12 Amine Oxide | 0.8 | 0.10 |
| Geraniol | 1.04 | 0.13 |
| Limonene | 0.52 | 0.065 |
| Eukalyptol | 0.52 | 0.065 |

To formulate the polar phase, all components are mixed together and then heated to 140° F. (45.8° C.). Separately, the lipid phase ingredients are heated, with mixing, to a temperature of about 140° F. until melted. The polar and lipid phase components are then combined in a stainless steel vessel and mixed with a Hobart Model 100-C mixer on the low speed setting while allowing the ingredients to cool slowly. Mixing is continued until the emulsion forms. Emulsion formation is evidenced by an increase in viscosity above 2000 centipoise as measured with a Lab-Line Instruments rotating disc viscometer.

B) Applying Emulsion to Carrier The emulsion is applied to the carrier materials according to the description in Example IV.

EXAMPLE VI

This example illustrates preparation of an article wherein the emulsion comprises significant levels of a polar material other than water in the internal phase.

A) Emulsion Preparation

A high internal phase emulsion (88.5% internal phase) is prepared from the ingredients shown in Table VI.

TABLE VI

| | Amount (gm) | Percentage |
|---|---|---|
| Lipid Phase Ingredients | | |
| Yellow Ceresine Wax (Strahl & Pitsch SP983) | 350 | 7% |
| Petrolatum (Fisher) | 50 | 1% |
| Dow Corning Q2-5200 emulsifier | 150 | 3% |
| Arlacel P-135 emulsifier from ICI | 25 | 0.5% |
| Polar Phase Ingredients | | |
| Sodium Carbonate (anhydrous) | 25 | 0.5% |
| Dantogard (preservative from Lonza) | 25 | 0.5% |
| Denatured ethanol (3A from VRW Scientific) | 2000 | 40% |
| Distilled Water | 2375 | 47.5% |

In formulating the polar phase component, the Dantogard, sodium carbonate and ethanol are added to the distilled water and then heated to 160° F. (71.1° C.). Separately, the lipid phase ingredients (Yellow ceresine wax, petrolatum, emulsifier Dow Corning Q2-5200 and emulsifier Arlacel P-135) are heated, with mixing, to a temperature of about 170° F. (77° C.) until melted. The polar internal phase and lipid external phase components are then combined in a stainless steel vessel and mixed with a Hobart Model 100 C mixer on the low speed setting while allowing the ingredients to cool slowly. Mixing is continued until the emulsion forms. Emulsion formation is evidenced by an increase in viscosity above 2000 centipoise as measured with a Lab-Line Instruments rotating disc viscometer.

B) Applying Emulsion to Carrier

The emulsion is applied to the carrier according to any of Examples I through IV.

What is claimed is:

1. An article, which comprises:
   a. a carrier comprising at least one polarphobic region; and
   b. an emulsion applied to the carrier, the emulsion comprising:
      (1) from about 2 to about 15% of a continuous solidified external lipid phase comprising a waxy lipid material having a melting point of about 30° C. or higher;
      (2) from about 82 to about 97% of an internal polar phase dispersed in the external lipid phase; and
      (3) an effective amount of an emulsifier capable of forming the emulsion when the external lipid phase is in a fluid state.

2. The article of claim 1 wherein the carrier further comprises at least one polarphilic substrate layer.

3. The article of claim 2 wherein the polarphilic substrate layer is a paper web.

4. The article of claim 3 wherein the at least one polarphobic region of the carrier comprises a material selected from the group consisting of a silicone crosslinking compound; a fluorochemical compound; a hydrophobic polymeric film; a layer of hydrophobic fibers; and mixtures thereof.

5. The article of claim 1 wherein the carrier is a polarphobic, polymeric film or a sheet of polarphobic fibers.

6. The article of claim 1 wherein the carrier comprises a nonwoven substrate treated with a polarphobic material selected from the group consisting of silicone crosslinking compound; a fluorochemical compound; and mixtures thereof.

7. The article of claim 6 wherein the polarphilic substrate is surface treated with the polarphobic material so that at least one surface of the substrate comprises numerous, discrete polarphobic regions dispersed in a continuous polarphilic region.

8. The article of claim 6 wherein the polarphilic substrate is surface treated with the polarphobic material so that at least one surface of the polarphilic substrate is rendered completely polarphobic.

9. The article of claim 4 wherein the carrier comprises a polarphobic, polymeric film.

10. The article of claim 9 wherein the carrier further comprises a distinct polarphilic substrate.

11. The article of claim 9 wherein the carrier comprises a polarphobic, polymeric film positioned between a first and a second polarphilic substrate layer.

12. The article of claim 11 wherein the emulsion is applied between the polarphobic film and the first polarphilic substrate layer.

13. The article of claim 1 wherein the emulsion comprises from about 6 to about 15% external lipid phase and from about 82 to about 91% internal polar phase.

14. The article of claim 1 wherein the waxy lipid material is selected from the group consisting of animal waxes, vegetable waxes, mineral waxes, synthetic waxes and mixtures thereof.

15. The article of claim 14 wherein the waxy lipid material is selected from the group consisting of beeswax, lanolin, candelilla, petrolatum, microcrystalline wax, yellow ceresine wax, white ozokerite, polyethylene waxes, and mixtures thereof.

16. The article of claim 1 wherein the emulsifier comprises from about 1 to about 10% of the emulsion, the emulsifier having an HLB value in the range of from about 2 to about 5 and being selected from group consisting of alkyl modified dimethicone copolyols, sorbitan esters of $C_{16}$–$C_{22}$ saturated, unsaturated and branched chain fatty acids, glyceryl monoesters of $C_{16}$–$C_{22}$ saturated, unsaturated and branched chain fatty acids, sucrose esters of $C_{16}$–$C_{22}$ saturated, unsaturated, and branched chain fatty acids, polyglycerol esters of $C_{16}$–$C_{22}$ saturated, unsaturated and branched chain fatty acids, and mixtures thereof.

17. The article of claim 16 wherein the emulsion further comprises a component selected from the group consisting of perfumes, antimicrobial actives, pharmaceutical actives, deodorants, opacifiers, astringents, skin moisturizers, and mixtures thereof.

18. An article, which comprises:
   a. a carrier comprising at least one polarphobic region; and
   b. an emulsion having a continuous external lipid phase and a dispersed polar internal phase applied to the carrier; wherein the emulsion is prepared by combining at least the following materials:
      (1) from about 2 to about 15% of a waxy lipid material having a melting point of about 30° C. or higher;
      (2) from about 82 to about 97% of a polar material; and
      (3) an effective amount of an emulsifier capable of forming the emulsion when the external lipid is in a fluid state;
   where the weight percent for each of components (1), (2) and (3) is determined from the amount combined relative to the total weight of the emulsion.

19. A process for applying an emulsion to a carrier comprising at least one polarphobic region, the process comprising the steps of:
   A. forming an emulsion comprising:
      (1) from about 2 to about 15% of a continuous external lipid phase comprising a waxy lipid material having a melting point of about 30° C. or higher;
      (2) from about 82 to about 97% of an internal polar phase dispersed in the external lipid phase; and
      (3) an effective amount of an emulsifier capable of forming the emulsion when the external lipid phase is in a fluid state;
   B. applying the emulsion to the carrier at a temperature sufficiently high such that the external lipid phase has a fluid or plastic consistency;
   C. cooling the applied emulsion to a temperature sufficiently low such that the external lipid phase solidifies.

20. The process of claim 19 wherein the emulsion is applied to the carrier by a step selected from the group consisting of spraying, printing, coating, extruding, and combinations thereof.

21. The process of claim 20 wherein the emulsion is applied to the carrier by flexible rotogravure coating.

22. The process of claim 19 wherein the emulsion is applied to the carrier at a constant volumetric flow rate.

23. The process of claim 19 wherein the carrier is a polarphobic, polymeric film positioned between a first and a second paper web, where the polarphobic film is adjacent the inner surface of each of the paper webs.

24. The process of claim 23 wherein the emulsion is applied i) to one surface of the polarphobic film, ii) to the inner surface of the first paper web, or iii) to the surface of the polarphobic film adjacent the first paper web and to the inner surface of the first paper web.

25. The process of claim 24 wherein a polar solution containing a detersive surfactant is applied the carrier.

26. An article, which comprises:
   a. a carrier comprising at least one hydrophobic region; and
   b. a water-in-lipid emulsion applied to the carrier, the emulsion comprising:
      (1) from about 2 to about 15% of a continuous solidified lipid phase comprising a waxy lipid material having a melting point of about 30° C. or higher;
      (2) from about 82 to about 97% of an internal water phase dispersed in the lipid phase; and
      (3) an effective amount of an emulsifier capable of forming the emulsion when the lipid phase is in a fluid state.

27. The article of claim 26 wherein the carrier further comprises at least one hydrophilic substrate layer.

28. The article of claim 27 wherein the hydrophilic substrate layer is a paper web.

29. The article of claim 28 wherein the at least one hydrophobic region of the carrier comprises a material selected from the group consisting of a silicone crosslinking compound; a fluorochemical compound; a hydrophobic polymeric film; a layer of hydrophobic fibers; and mixtures thereof.

30. The article of claim 26 wherein the carrier is a hydrophobic, polymeric film or a sheet of hydrophobic fibers.

31. The article of claim 26 wherein the carrier comprises a nonwoven substrate treated with a hydrophobic material selected from the group consisting of silicone crosslinking compound; a fluorochemical compound; and mixtures thereof.

32. The article of claim 31 wherein the hydrophilic substrate is surface treated with the hydrophobic material so that at least one surface of the substrate comprises numerous, discrete hydrophobic regions dispersed in a continuous hydrophilic region.

33. The article of claim 32 wherein the hydrophilic substrate is surface treated with the hydrophobic material so that at least one surface of the hydrophilic substrate is rendered completely hydrophobic.

34. The article of claim 26 wherein the emulsion comprises from about 5 to about 15% lipid phase and from about 82 to about 92% water phase.

35. The article of claim 26 wherein the waxy lipid material is selected from the group consisting of animal waxes, vegetable waxes, mineral waxes, synthetic waxes and mixtures thereof.

36. The article of claim 26 wherein the emulsifier comprises from about 1 to about 10% of the emulsion, the emulsifier having an HLB value in the range of from about 2 to about 5 and being selected from group consisting of alkyl modified dimethicone copolyols, sorbitan esters of $C_{16}$–$C_{22}$ saturated, unsaturated and branched chain fatty acids, glyceryl monoesters of $C_{16}$–$C_{22}$ saturated, unsaturated and branched chain fatty acids, sucrose esters Of $C_{16}$–$C_{22}$ saturated, unsaturated, and branched chain fatty acids, polyglycerol esters of $C_{16}$–$C_{22}$ saturated, unsaturated and branched chain fatty acids, and mixtures thereof.

37. An article, which comprises:
   a. a carrier comprising at least one hydrophobic region; and
   b. a water-in-lipid emulsion applied to the carrier; wherein the emulsion is prepared by combining at least the following materials:

(1) from about 2 to about 15% of a waxy lipid material having a melting point of about 30° C. or higher;
(2) from about 82 to about 97% of water; and
(3) an effective amount of an emulsifier capable of forming the emulsion when the lipid is in a fluid state;

where the weight percent for each of components (1), (2) and (3) is determined from the amount combined relative to the total weight of the emulsion.

38. An article, which comprises:
a. a carrier comprising a polarphobic, polymeric film positioned between a first and a second polarphilic substrate layer; and
b. an emulsion applied to the carrier, the emulsion comprising:
   (1) from about 2 to about 60% of a continuous solidified external lipid phase comprising a waxy lipid material having a melting point of about 30° C. or higher;
   (2) from about 39 to about 97% of an internal polar phase dispersed in the external lipid phase; and
   (3) an effective amount of an emulsifier capable of forming the emulsion when the external lipid phase is in a fluid state.

39. The article of claim 38 wherein the first and second polarphilic substrate layers are both paper webs.

40. The article of claim 39 wherein the emulsion is applied between the polarphobic film and the first paper web.

41. The article of claim 40 wherein the second paper web is treated with a polar solution containing a detersive surfactant.

42. The article of claim 38 wherein the first polarphilic substrate layer is a paper web and the second polarphilic substrate layer is a nonwoven material.

43. The article of claim 42 wherein the emulsion is applied only between the polarphobic film and the nonwoven material.

44. The article of claim 38 wherein the polarphilic substrate layers are each independently selected from the group consisting of woven materials, nonwoven materials, foams, sponges, battings, balls, puffs, and films.

45. The article of claim 38 wherein the emulsion comprises from about 5 to about 30% external lipid phase and from about 67 to about 92% internal polar phase.

46. The article of claim 45 wherein the emulsion comprises from about 6 to about 15% external lipid phase and from about 82 to about 91% internal polar phase.

47. The article of claim 38 wherein the waxy lipid material has a melting point in the range of from about 40° to about 80° C.

48. The article of claim 47 wherein the waxy lipid material has a melting point in the range of from about 600 to about 70° C.

49. The article of claim 38 wherein the waxy lipid material is selected from the group consisting of animal waxes, vegetable waxes, mineral waxes, synthetic waxes and mixtures thereof.

50. The article of claim 49 wherein the waxy lipid material is selected from the group consisting of beeswax, lanolin, candelilla, petrolatum, microcrystalline wax, yellow ceresine wax, white ozokerite, polyethylene waxes, and mixtures thereof.

51. The article of claim 38 wherein the emulsifier comprises from about 1 to about 10% of the emulsion, the emulsifier having an HLB value in the range of from about 2 to about 5 and being selected from group consisting of alkyl modified dimethicone copolyols, sorbitan esters of $C_{16}$–$C_{22}$ saturated, unsaturated and branched chain fatty acids, glyceryl monoesters of $C_{16}$–$C_{22}$ saturated, unsaturated and branched chain fatty acids, sucrose esters of $C_{12}$–$C_{22}$ saturated, unsaturated, and branched chain fatty acids, polyglycerol esters of $C_{16}$–$C_{22}$ saturated, unsaturated and branched chain fatty acids, and mixtures thereof.

52. The article of claim 51 wherein the emulsion further comprises a component selected from the group consisting of perfumes, antimicrobial actives, pharmaceutical actives, deodorants, opacifiers, astringents, skin moisturizers, and mixtures thereof.

* * * * *

UNITED STATES PATENT AND TRADEMARK OFFICE
CERTIFICATE OF CORRECTION

PATENT NO. : 6,001,381
DATED : December 14, 1999
INVENTOR(S) : Gordon et al.

It is certified that error appears in the above-identified patent and that said Letters Patent is hereby corrected as shown below:

Title page,
Item [57], ABSTRACT, line 3, "polarpliobic" should read -- polarphobic --.

Column 3,
Line 22, "surf ace" should read -- surface --.
Line 27, "tile" should read -- the --.

Signed and Sealed this

Seventh Day of May, 2002

Attest:

JAMES E. ROGAN
*Attesting Officer*     *Director of the United States Patent and Trademark Office*